(12) United States Patent
Li et al.

(10) Patent No.: US 7,524,880 B2
(45) Date of Patent: Apr. 28, 2009

(54) CRYSTALLINE FORM OF A SUBSTITUTED PYRROLIDINE COMPOUND

(75) Inventors: Li Li, Sunnyvale, CA (US); Robert Chao, Santa Clara, CA (US); Adam Hughes, Belmont, CA (US); Yu-Hua Ji, Redwood City, CA (US); Davar Khossravi, San Mateo, CA (US); Weijiang Zhang, Concord, CA (US)

(73) Assignee: Theravance, Inc., South San Francisco, CA (US)

( * ) Notice: Subject to any disclaimer, the term of this patent is extended or adjusted under 35 U.S.C. 154(b) by 239 days.

(21) Appl. No.: 11/148,728

(22) Filed: Jun. 9, 2005

(65) Prior Publication Data

US 2005/0277688 A1 Dec. 15, 2005

Related U.S. Application Data

(60) Provisional application No. 60/578,647, filed on Jun. 10, 2004.

(51) Int. Cl.
*A61K 31/40* (2006.01)
*C07D 207/09* (2006.01)

(52) U.S. Cl. ...................... 514/428; 548/571

(58) Field of Classification Search ................ 514/428; 548/571
See application file for complete search history.

(56) References Cited

U.S. PATENT DOCUMENTS

| | | | |
|---|---|---|---|
| 3,247,222 A | 4/1966 | Lunsford | |
| 3,732,247 A | 5/1973 | Helsley et al. | |
| 3,903,137 A | 9/1975 | Miura et al. | |
| 4,002,766 A | 1/1977 | Welstead, Jr. | |
| 5,750,540 A | 5/1998 | Tsuchiya et al. | |
| 6,433,027 B1 | 8/2002 | Bozung et al. | |
| 6,613,804 B2 * | 9/2003 | Chan et al. | 514/601 |
| 6,693,202 B1 | 2/2004 | Aggen et al. | |
| 7,183,292 B2 * | 2/2007 | Mammen et al. | 514/315 |
| 2003/0018019 A1 | 1/2003 | Meade et al. | |
| 2004/0122014 A1 | 6/2004 | Mammen et al. | |
| 2004/0254219 A1 | 12/2004 | Mammen et al. | |
| 2005/0026954 A1 | 2/2005 | Mammen et al. | |
| 2005/0113413 A1 | 5/2005 | Wilson et al. | |
| 2006/0287369 A1 | 12/2006 | Mammen et al. | |

FOREIGN PATENT DOCUMENTS

EP 0 178 946 A2 4/1986

OTHER PUBLICATIONS

Bauer et al. "Ritonavir: An Extrordinary Example of Conformational Polymorphism" Pharmaceutical Research, 2001, vol. 18, No. 6, pp. 859-866.*
Drugs of the Future, 7(4), pp. 227-228 (1982).
Graul et al., "Darifenacin", Drugs of the Future, 21(11), pp. 1105-1108 (1996).
Taniguchi et al., "Agents for the Treatment of Overactive Detrusor, VI.[1a)] Synthesis and Pharmacological Properties of Acetamide Derivatives Bearing Cyclic Amines in N-Substitutents", Chem. Pharm. Bull, 42(1), pp. 74-84 (1994).

* cited by examiner

*Primary Examiner*—Rei-Tsang Shiao
*Assistant Examiner*—Joseph R Kosack
(74) *Attorney, Agent, or Firm*—Jeffrey A. Hagenah; Shelley Eberle

(57) ABSTRACT

The invention provides a crystalline naphthalene-1,5-disulfonic acid salt of 2-[(S)-1-(8-methylaminooctyl)pyrrolidin-3-yl]-2,2-diphenylacetamide or a solvate thereof. This invention also provides pharmaceutical compositions comprising the salt or prepared using the salt; processes and intermediates for preparing the salt; and methods of using the salt to treat a pulmonary disorder.

13 Claims, 5 Drawing Sheets

CRYSTALLINE FORM OF A SUBSTITUTED PYRROLIDINE COMPOUND

CROSS-REFERENCE TO RELATED APPLICATIONS

This application claims the benefit of U.S. Provisional Application No. 60/578,647, filed on Jun. 10, 2004; the entire disclosure of which is incorporated herein by reference in its entirety.

BACKGROUND OF THE INVENTION

1. Field of the Invention

The present invention relates to a novel crystalline naphthalene-1,5-disulfonic acid salt of a substituted pyrrolidine compound that is useful for treating pulmonary disorders. This invention also relates to pharmaceutical compositions comprising the crystalline compound or prepared from the crystalline compound, processes and intermediates for preparing the crystalline compound and methods of using the crystalline compound to treat a pulmonary disorder.

2. State of the Art

Commonly-assigned U.S. Patent Publication No. 2004/0254219 to Mathai et al., discloses novel substituted pyrrolidine compounds that are useful for treating pulmonary disorders, such as chronic obstructive pulmonary disease (COPD) and asthma. In particular, the compound, 2-[(S)-1-(8-methylaminooctyl)pyrrolidin-3-yl]-2,2-diphenylacetamide is specifically disclosed in this application as possessing muscarinic antagonist activity.

The chemical structure of 2-[(S)-1-(8-methylaminooctyl)pyrrolidin-3-yl]-2,2-diphenylacetamide is represented by formula I:

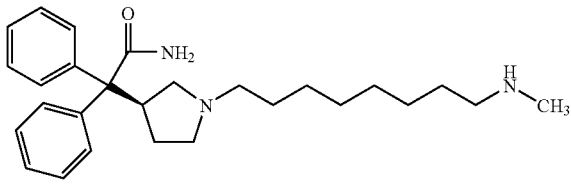

I

Therapeutic agents useful for treating pulmonary disorders are advantageously administered directly into the respiratory tract by inhalation. In this regard, several types of pharmaceutical inhalation devices have been developed for administering therapeutic agents by inhalation including dry powder inhalers (DPI), metered-dose inhalers (MDI) and nebulizer inhalers. When preparing pharmaceutical compositions and formulations for use in such devices, it is highly desirable to have a crystalline form of a pharmaceutically acceptable salt the active agent that is neither hygroscopic nor deliquescent and which has a relatively high melting point (i.e. greater than about 150° C.) thereby allowing the material to be micronized without significant decomposition.

No salt forms of the compound of formula I, 2-[(S)-1-(8-methylaminooctyl)pyrrolidin-3-yl]-2,2-diphenylacetamide, have been reported previously. Accordingly, a need exists for a stable, non-deliquescent salt form of the compound of formula I which has an acceptable level of hygroscopicity and a relatively high melting point.

SUMMARY OF THE INVENTION

The present invention provides a crystalline naphthalene-1,5-disulfonic acid salt of the compound of formula I or a solvate thereof. This crystalline naphthalene-1,5-disulfonic acid salt has been found not to be deliquescent, even when exposed to atmospheric moisture. Additionally, the crystalline salt of this invention has an acceptable level of hygroscopicity and a very high melting point, greater than about 200° C.

Among other uses, a crystalline naphthalene-1,5-disulfonic acid salt of the compound of formula I is useful for preparing pharmaceutical compositions for treating pulmonary disorders. However, once the crystalline salt of this invention has been formulated, it may no longer be in crystalline form, i.e., the salt may be dissolved in a suitable carrier. Accordingly, in another of its composition aspects, the present invention provides a pharmaceutical composition comprising a pharmaceutically acceptable carrier and a naphthalene-1,5-disulfonic acid salt of the compound of formula I or a solvate thereof.

In a particular embodiment, the pharmaceutical composition of this invention further comprises a steroidal anti-inflammatory agent, such as a corticosteroid; a $\beta_2$ adrenergic receptor agonist; a phosphodiesterase-4 inhibitor; or a combination thereof.

In another embodiment, this invention provides a pharmaceutical composition comprising an aqueous isotonic saline solution comprising a naphthalene-1,5-disulfonic acid salt of the compound of formula I, wherein the solution has a pH in the range of from about 4 to about 6.

In one embodiment, this invention provides a drug delivery device comprising a dry powder inhaler containing a pharmaceutical composition comprising a pharmaceutically acceptable carrier and a naphthalene-1,5-disulfonic acid salt of the compound of formula I or a solvate thereof.

The compound of formula I has muscarinic antagonist activity. Accordingly, a naphalene-1,5-disulfonic acid salt of this invention is useful for treating pulmonary disorders, such as asthma and chronic obstructive pulmonary disease.

Accordingly, in one of its method aspects, this invention provides a method for treating a pulmonary disorder, the method comprising administering to a patient a therapeutically effective amount of a naphthalene-1,5-disulfonic acid salt of the compound of formula I or a solvate thereof.

Additionally, in another of its method aspects, this invention provides a method of producing bronchodilation in a patient, the method comprising administering by inhalation to the patient a bronchodilation-producing amount of a naphthalene-1,5-disulfonic acid salt of the compound of formula I or a solvate thereof.

This invention also provides a method of treating chronic obstructive pulmonary disease or asthma, the method comprising administering to a patient a therapeutically effective amount of a naphthalene-1,5-disulfonic acid salt of the compound of formula I or a solvate thereof.

In another one of its method aspects, this invention is directed to a method for antagonizing a muscarinic receptor in a mammal comprising administering to the mammal, a muscarinic receptor antagonizing amount of a naphthalene-1,5-disulfonic acid salt of the compound of formula I or a solvate thereof.

This invention is also directed to processes for preparing a crystalline naphthalene-1,5-disulfonic acid salt of the compound of formula I.

Accordingly, in another of its method aspects, this invention provides a process for preparing a crystalline naphthalene-1,5-disulfonic acid salt of the compound of formula I or a solvate thereof; the process comprising contacting 2-[(S)-1-(8-methylaminooctyl)pyrrolidin-3-yl]-2,2-diphenylacetamide with naphthalene-1,5-disulfonic acid.

In yet another of its method aspects, this invention provides a process for preparing a crystalline naphthalene-1,5-disulfonic acid salt of the compound of formula I or a solvate thereof; the process comprising contacting 2-{(S)-1-[8-(N-tert-butoxycarbonyl-N-methylamino)octyl]-pyrrolidin-3-yl}-2,2-diphenylacetamide with naphthalene-1,5-disulfonic acid.

Additionally, this invention is directed to a process for purifying 2-[(S)-1-(8-methylaminooctyl)pyrrolidin-3-yl]-2,2-diphenylacetamide; the process comprising forming a crystalline naphthalene-1,5-disulfonic acid salt of the compound of formula I. This invention is also directed to the products prepared by the processes described herein.

This invention is also directed to a naphthalene-1,5-disulfonic acid salt of the compound of formula I or a solvate thereof for use in therapy or as a medicament.

Additionally, this invention is directed to the use of a naphthalene-1,5-disulfonic acid salt of the compound of formula I or a solvate thereof for the manufacture of a medicament; especially for the manufacture of a medicament for the treatment of a pulmonary disorder or for antagonizing a muscarinic receptor in a mammal.

This invention is also directed to a crystalline naphthalene-1,5-disulfonic acid salt of the compound of formula I or a solvate thereof, in micronized form; and to pharmaceutical compositions comprising a pharmaceutically acceptable carrier and this micronized form.

BRIEF DESCRIPTION OF THE DRAWINGS

Various aspects of the present invention are illustrated by reference to the accompanying drawings.

DETAILED DESCRIPTION OF THE INVENTION

Figure 1:
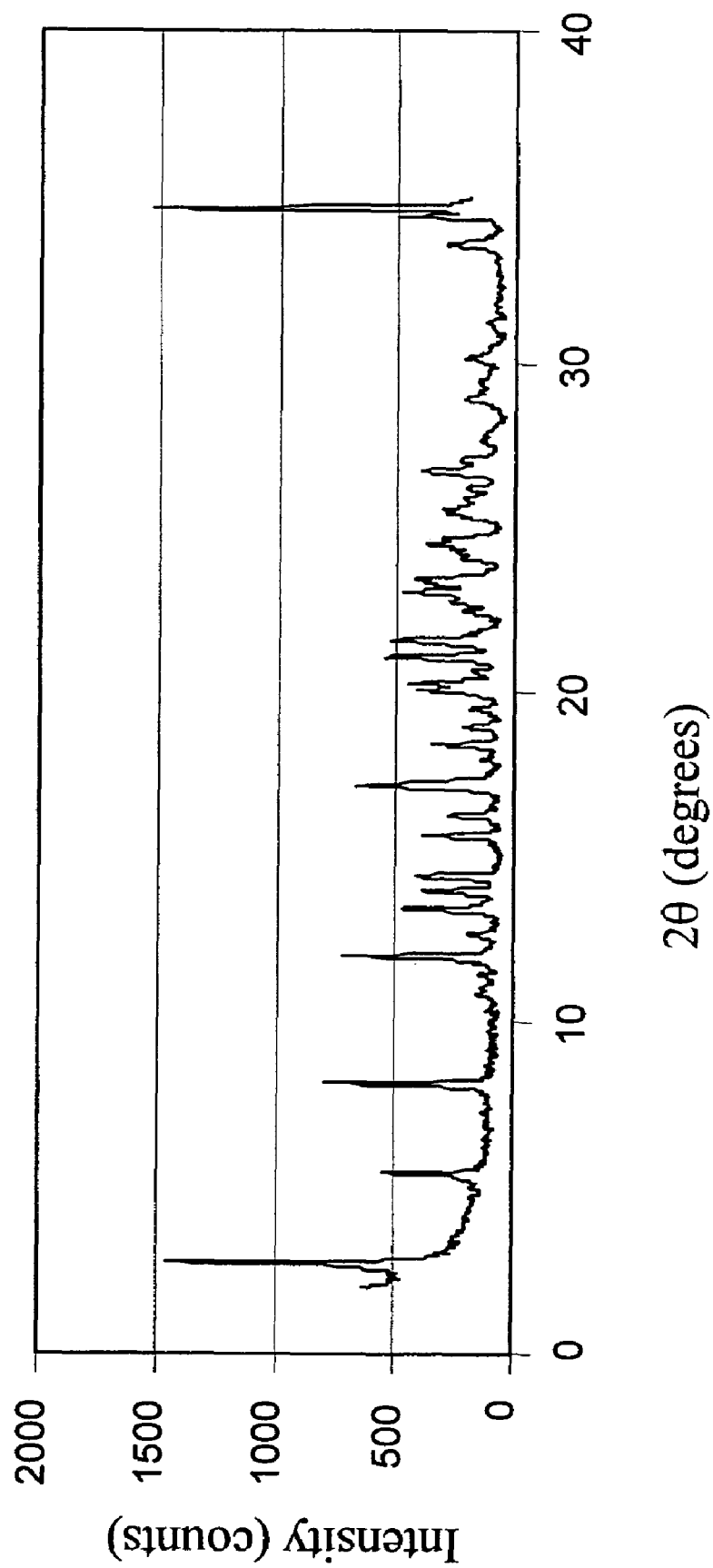
FIG. 1 shows a powder x-ray diffraction (PXRD) pattern of a crystalline naphthalene-1,5-disulfonic acid salt of 2-[(S)-1-(8-methylaminooctyl)pyrrolidin-3-yl]-2,2-diphenylacetamide.

This invention provides a crystalline naphthalene-1,5-disulfonic acid salt of 2-[(S)-1-(8-methylaminooctyl)pyrrolidin-3-yl]-2,2-diphenylacetamide or a solvate thereof. The active agent in this salt (i.e., the compound of formula I) contains one chiral center having the (S) configuration. However, it will be understood by those skilled in the art that minor amounts of the (R) stereoisomer may be present in the compositions of this invention unless otherwise indicated, provided that the utility of the composition as a whole is not eliminated by the presence of such an isomer.

The compound of formula I has been named using the commercially-available AutoNom software (MDL, San Leandro, Calif.). Additionally, naphthalene-1,5-disulfonic acid salts are also sometimes referred to as napadisylate salts.

Definitions

When describing the compounds, compositions, methods and processes of this invention, the following terms have the following meanings unless otherwise indicated.

The term "solvate" means a crystal form, where molecules of solvent are incorporated in the unit cell of the crystal lattice, i.e. a naphthalene-1,5-disulfonic acid salt of the compound of formula I, and molecules of a solvent. The solvate may include one or more molecules of solvent, but the number of solvent molecules may also be a fraction of one, such as one-half or one-fourth. Solvates typically have a substantially fixed molar ratio of solute and solvent. This term also includes clathrates, including clathrates with water. Representative solvents include, by way of example, water, methanol, ethanol, isopropanol, acetic acid and the like. When the solvent molecule in a solvate crystal is water, the crystal is called a hydrate, which is one class of solvates.

The term "therapeutically effective amount" means an amount sufficient to effect treatment when administered to a patient in need of treatment.

The term "treating" or "treatment" as used herein means the treating or treatment of a disease or medical condition (such as COPD) in a patient, such as a mammal (particularly a human) that includes:

(a) preventing the disease or medical condition from occurring, i.e., prophylactic treatment of a patient;

(b) ameliorating the disease or medical condition, i.e., eliminating or causing regression of the disease or medical condition in a patient;

(c) suppressing the disease or medical condition, i.e., slowing or arresting the development of the disease or medical condition in a patient; or (d) alleviating the symptoms of the disease or medical condition in a patient.

The term "unit dosage form" refers to a physically discrete unit suitable for dosing a patient; i.e., each unit containing a predetermined quantity of a salt of this invention calculated to produce the desired therapeutic effect either alone or in combination with one or more additional units. For example, such unit dosage forms may be capsules, tablets, pills, powder blends in individual blister packs, loose powder compacts, and the like.

Naphthalene-1,5-disulfonic Acid Salts of the Invention

A crystalline naphthalene-1,5-disulfonic acid salt of 2-[(S)-1-(8-methylaminooctyl)pyrrolidin-3-yl]-2,2-diphenylacetamide of this invention can be prepared from 2-[(S)-1-(8-methylaminooctyl)pyrrolidin-3-yl]-2,2-diphenylacetamide and naphthalene-1,5-disulfonic acid.

A naphthalene-1,5-disulfonic acid salt of this invention typically contains between about 0.75 and about 1.30 molar equivalents of naphthalene-1,5-disulfonic acid per molar equivalent of the compound of formula I; including between about 0.90 and about 1.30 molar equivalents of naphthalene-1,5-disulfonic acid per molar equivalent of the compound of formula I.

The molar ratio of naphthalene-1,5-disulfonic acid to 2-[(S)-1-(8-methylaminooctyl)pyrrolidin-3-yl]-2,2-diphenylacetamide can be readily determined by various methods available to those skilled in the art. For example, such molar ratios can be readily determined by $^1$H NMR. Alternatively, elemental analysis and HPLC methods can be used to determine the molar ratio.

The 2-[(S)-1-(8-methylaminooctyl)pyrrolidin-3-yl]-2,2-diphenylacetamide employed in this invention can be readily prepared from commercially available starting materials and reagents using the procedures described in the Examples below; or using the procedures described in U.S. Patent Publication No. 2004/0254219 to Mathai et al.

Naphthalene-1,5-disulfonic acid (also known as Armstrong's Acid) is commercially available from, for example, Aldrich, Milwaukee, Wis. In one embodiment, the naphthalene-1,5-disulfonic acid employed in preparing the salts of this invention is a tetrahydrate. In a particular embodiment, the naphthalene-1,5-disulfonic acid tetrahydrate has a purity greater than or equal to 97% (as determined by HPLC). If desired, the naphthalene-1,5-disulfonic acid tetrahydrate employed in this invention can be recrystallized from, for example, acetonitrile prior to use.

To prepare a crystalline salt of this invention, 2-[(S)-1-(8-methylaminooctyl)pyrrolidin-3-yl]-2,2-diphenylacetamide is typically contacted with about 0.75 to about 1.3 molar equivalents of naphthalene-1,5-disulfonic acid. Generally, this reaction is conducted in an inert diluent at a temperature ranging from about 0° C. to about 60° C.; including about 20° C. to about 55° C., such as about 25° C. to about 50° C. Suitable inert diluents for this reaction include, but are not limited to, methanol, ethanol, isopropanol, isobutanol, ethyl acetate and the like optionally containing water. In a particular embodiment, a solution of naphthalene-1,5-disulfonic acid in a mixture of ethanol or isopropanol and water is added to an equal volume of 2-[(S)-1-(8-methylaminooctyl)pyrrolidin-3-yl]-2,2-diphenylacetamide in isopropanol.

Alternatively, the crystalline salt of this invention can be prepared by contacting 2-{(s)-1-[8-(N-tert-butoxycarbonyl-N-methylamino)octyl]pyrrolidin-3-yl}-2,2-diphenylacetamide with about 1 to about 2.1 molar equivalents of naphthalene-1,5-disulfonic acid. Generally, this reaction is conducted in an inert diluent at a temperature ranging from about 25° C. to about 100° C.; including about 70° C. to about 90° C., such as about 80° C. to about 85° C. Suitable inert diluents for this reaction include, but are not limited to, isopropanol and the like optionally containing water. In a particular embodiment, a solution of 2-{(S)-1-[8-(N-tert-butoxycarbonyl-N-methylamino)octyl]-pyrrolidin-3-yl}-2,2-diphenylacetamide and about 1.9 to about 2.1 molar equivalents of naphthalene-1,5-disulfonic acid tetrahydrate in isopropanol containing about 2% to about 10% water by volume is heated at about 80° C. to about 85° C. for about 2 to about 6 hours. In this reaction, the ratio of grams of 2-{(S)-1-[8-(N-tert-butoxycarbonyl-N-methylamino)octyl]-pyrrolidin-3-yl}-2,2-diphenylacetamide to milliliters of isopropanol/water is about 1:45 to about 1:55, including about 1:48 to about 1:52 or about 1:50.

Upon completion of the reaction, the crystalline salt can be isolated from the reaction mixture by any conventional means, such as precipitation, concentration, centrifugation and the like.

Among other advantages, it has been discovered that forming a crystalline naphthalene-1,5-disulfonic acid salt of the compound of formula I is useful for purifying the compound of formula I. Generally, a crystalline naphthalene-1,5-disulfonic acid salt of this invention has a purity greater than 95%; and typically greater than 98%, as determined by high performance liquid chromatography.

In one embodiment, the crystalline naphthalene-1,5-disulfonic acid salt of the present invention is characterized by a powder x-ray diffraction (PXRD) pattern having two or more diffraction peaks at 2θ values selected from 5.45±0.2, 8.17±0.2, 12.02±0.2, 13.46±0.2, 14.00±0.2, 14.46±0.2, 15.69±0.2, 16.31±0.2, 17.22±0.2, 18.45±0.2, 20.13±0.2, 21.11±0.2, and 21.62±0.2. In particular, in this embodiment, the crystalline form is characterized by a powder x-ray diffraction pattern comprising diffraction peaks at 2θ values of 8.17±0.2, 12.02±0.2, and 17.22±0.2.

As is well known in the field of powder x-ray diffraction, relative peak heights of PXRD spectra are dependent on a number of factors relating to sample preparation and instrument geometry, while peak positions are relatively insensitive to experimental details. Thus, in one embodiment, the crystalline naphthalene-1,5-disulfonic acid salt of the compound of formula I is characterized by a powder x-ray diffraction pattern in which the peak positions are substantially in accordance with those shown in FIG. 1.

Figure 4:
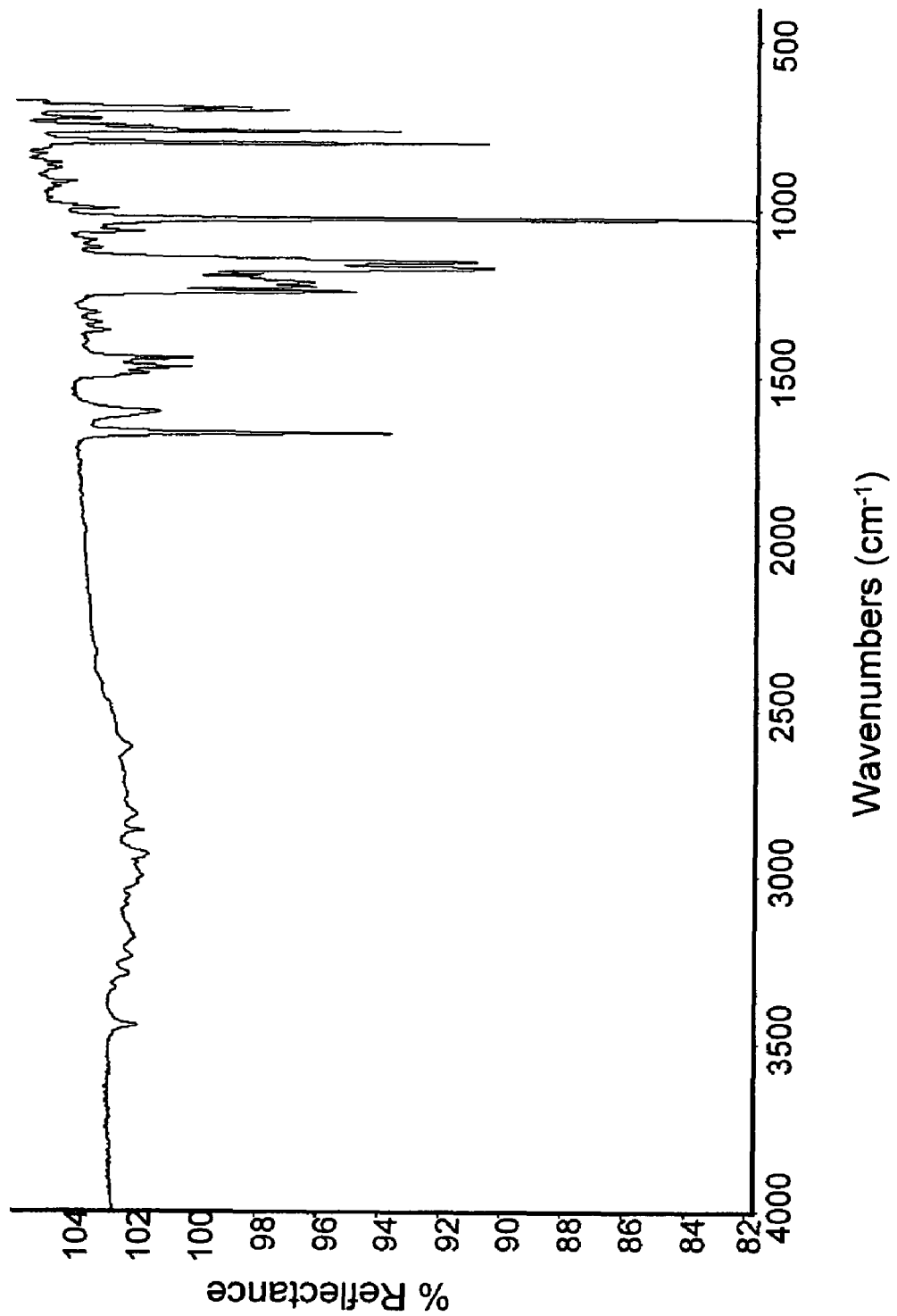
FIG. 4 shows an infrared (IR) absorption spectra for a crystalline naphthalene-1,5-disulfonic acid salt of 2-[(S)-1-(8-methylaminooctyl)pyrrolidin-3-yl]-2,2-diphenylacetamide.

In another embodiment, the crystalline naphthalene-1,5-disulfonic acid salt of the compound of formula I is characterized by its infrared (IR) absorption spectrum which shows significant absorption bands at about 696, 704, 765, 800, 1028, 1154, 1172, 1191, 1217, 1230, 1245, and 1669 cm$^{-1}$, as illustrated in FIG. 4.

Figure 2:
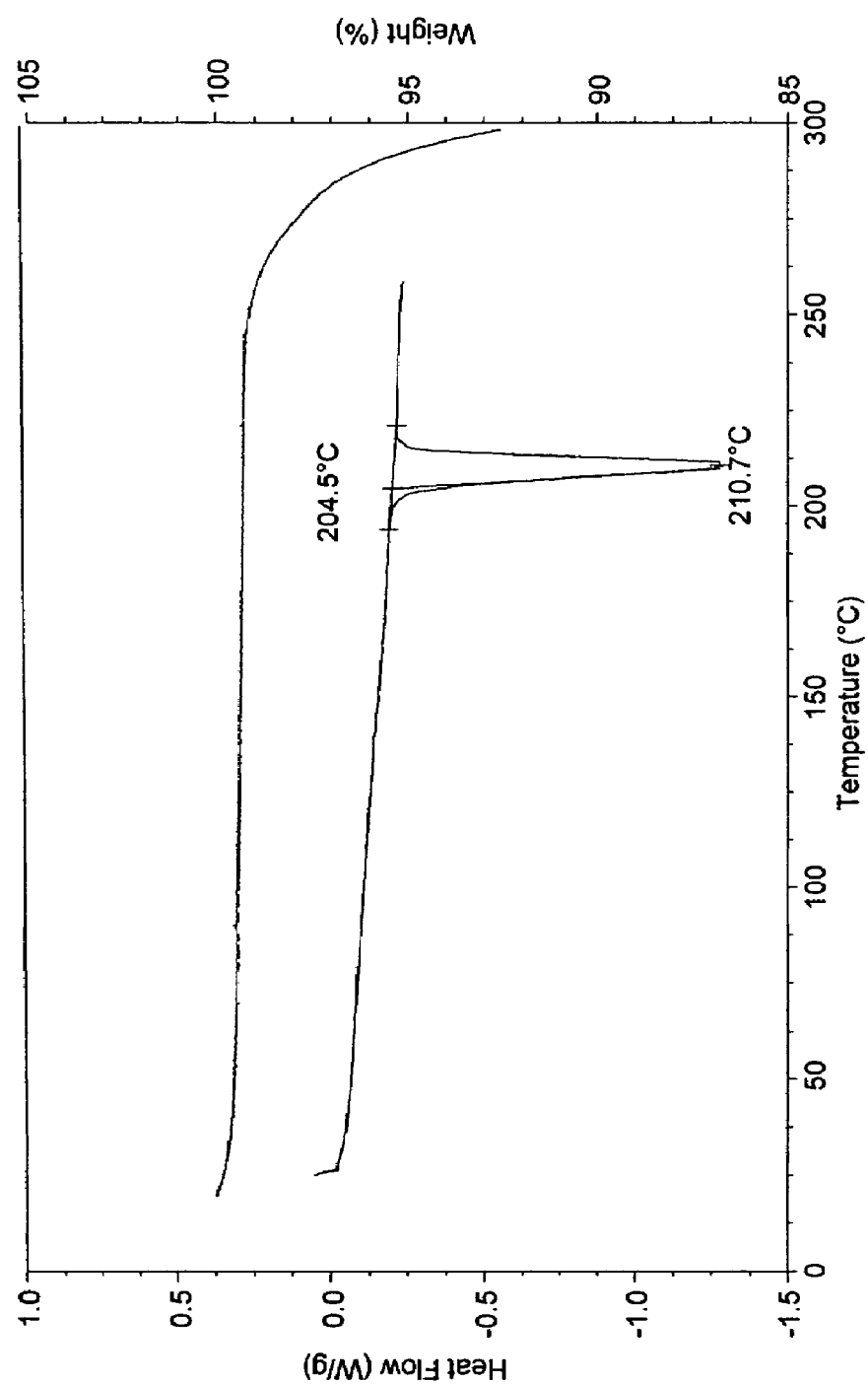
FIG. 2 shows a differential scanning calorimetry (DSC) trace and a thermal gravimetric analysis (TGA) trace for a crystalline naphthalene-1,5-disulfonic acid salt of 2-[(S)-1-(8-methylaminooctyl)pyrrolidin-3-yl]-2,2-diphenylacetamide.

In yet another embodiment, a crystalline naphthalene-1,5-disulfonic acid salt of the compound of formula I is characterized by its differential scanning calorimetry (DSC) trace which shows an onset of endothermic heat flow at about 200° C., as illustrated in FIG. 2.

A crystalline naphthalene-1,5-disulfonic acid salt of the compound of formula I has been demonstrated to have a reversible sorption/desorption profile with an acceptable, moderate level of hygroscopicity (i.e., less than 2% weight gain when exposed to up to 90% relative humidity).

Additionally, the crystalline naphthalene-1,5-disulfonic acid salt of the compound of formula I has been found to be stable upon exposure to elevated temperatures and humidity. For example, after storage for 28 days at 40° C. and 75% relative humidity, analysis by high pressure liquid chromatography (HPLC) showed no detectable chemical degradation (i.e., less than 0.5% degradation). Similar studies conducted after 6 months storage under the same conditions also showed no detectable chemical degradation.

These properties of the salts of this invention are further illustrated in the Examples below.

Pharmaceutical Compositions and Formulations

The crystalline naphthalene-1,5-disulfonic acid salt of the compound of formula I is typically administered to a patient in the form of a pharmaceutical composition or formulation. The crystalline salt itself may be administered in a pharmaceutical composition, or the crystalline salt may be used in the preparation of a pharmaceutical composition. Thus, it will be understood by those skilled in the art that, once the crystalline salt of this invention has been formulated, it may no longer be in crystalline form, i.e., the salt may be dissolved in a suitable carrier.

Such pharmaceutical compositions may be administered to the patient by any acceptable route of administration including, but not limited to, inhaled, oral, nasal, topical (including transdermal) and parenteral modes of administration.

Accordingly, in one of its compositions aspects, this invention is directed to a pharmaceutical composition comprising a pharmaceutically acceptable carrier or excipient and a naphthalene-1,5-disulfonic acid salt of 2-[(S)-1-(8-methylaminooctyl)pyrrolidin-3-yl]-2,2-diphenylacetamide or a solvate thereof. Optionally, such pharmaceutical compositions may contain other therapeutic and/or formulating agents if desired.

The pharmaceutical compositions of this invention typically contain a therapeutically effective amount of a naphthalene-1,5-disulfonic acid salt of 2-[(S)-1-(8-methylaminooctyl)pyrrolidin-3-yl]-2,2-diphenylacetamide or a solvate thereof. Generally, such pharmaceutical compositions will contain from about 0.001 to about 95% by weight of the active agent; including, from about 0.001 to about 30% by weight; such as from about 0.001 to about 10% by weight of the active agent.

Any conventional carrier or excipient may be used in the pharmaceutical compositions of this invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in Remington: The Science and Practice of Pharmacy, 20$^{th}$ Edition, Lippincott Williams & White, Baltimore, Md. (2000); and H. C. Ansel et al., Pharmaceutical Dosage Forms and Drug Delivery Systems, 7$^{th}$ Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter- and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as citrate and phosphate buffer solutions; (15) alginic acid; (16) pyrogen-free water; (17) isotonic saline; (18) Ringer's solution; (19) ethyl alcohol; (20) compressed propellant gases, such as chlorofluorocarbons and hydrofluorocarbons; and (21) other non-toxic compatible substances employed in pharmaceutical compositions.

The pharmaceutical compositions of this invention are typically prepared by thoroughly and intimately mixing or blending a salt of this invention with a pharmaceutically acceptable carrier and one or more optional ingredients. If necessary or desired, the resulting uniformly blended mixture can then be shaped or loaded into tablets, capsules, pills, unit dose blister packs, canisters, cartridges, dispensers and the like using conventional procedures and equipment.

In one embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI), or a similar delivery device.

In a specific embodiment of this invention, the pharmaceutical composition comprising the salt of this invention is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the salt is typically dissolved in a suitable carrier to form a solution. Suitable nebulizer devices are provided commercially, for example, by PARI GmbH (Starnberg, German). Other nebulizer devices include Respimat (Boehringer Ingelheim) and those disclosed, for example, in U.S. Pat. No. 6,123,068 to Lloyd et al. and WO 97/12687 (Eicher et al.).

A representative pharmaceutical composition for use in a nebulizer inhaler comprises an aqueous solution comprising from about 0.05 μg/mL to about 10 mg/mL of a salt of this invention. In one embodiment, the aqueous nebulizer formulation is isotonic. In one embodiment, the aqueous nebulizer formulation has a pH in the range of from about 4 to about 6. In a particular embodiment, the aqueous nebulizer formulation is buffered with citrate buffer, for example, to a pH of about 5. In another particular embodiment, the aqueous nebulizer formulation contains from about 0.1 mg/mL to about 8 mg/mL free base equivalents of 2-[(S)-1-(8-methylaminooctyl)pyrrolidin-3-yl]-2,2-diphenylacetamide.

The pharmaceutical composition comprising the salt of this invention may also be administered by inhalation using a dry powder inhaler. Thus, in another specific embodiment, the invention provides a drug delivery device comprising a dry powder inhaler containing a pharmaceutical composition comprising a pharmaceutically acceptable carrier and a naphthalene-1,5-disulfonic acid salt of the compound of formula I or a solvate thereof. Such dry powder inhalers typically administer the salt as a free-flowing powder that is dispersed in a patient's air-stream during inspiration. In order to achieve a free flowing powder, the salt is typically formulated with a suitable excipient such as lactose or starch. Typically, the salt is micronized and combined with a suitable carrier to form a suspension of micronized particles of respirable size, where "micronized particles" or "micronized form" means at least about 90% of the particles have a diameter of less than about 10 μm. Other methods of reducing particle size may also be used, such as fine milling, chopping, crushing, grinding, milling, screening, trituration, pulverization, and so forth, as long as the desired particle size can be obtained.

A representative pharmaceutical composition for use in a dry powder inhaler comprises dry lactose having a particle size between about 1 μm and about 100 μm and micronized particles of the salt of this invention.

Such a dry powder formulation can be made, for example, by combining the lactose with the salt and then dry blending the components. Alternatively, if desired, the salt can be formulated without an excipient. The pharmaceutical composition is then typically loaded into a dry powder dispenser, or into inhalation cartridges or capsules for use with a dry powder delivery device.

Examples of dry powder inhaler delivery devices include Diskhaler (GlaxoSmithKline, Research Triangle Park, N.C.) (see, e.g., U.S. Pat. No. 5,035,237 to Newell et al.); Diskus (GlaxoSmithKline) (see, e.g., U.S. Pat. No. 6,378,519 to Davies et al.); Turbuhaler (AstraZeneca, Wilmington, Del.) (see, e.g., U.S. Pat. No. 4,524,769 to Wetterlin); Rotahaler (GlaxoSmithKline) (see, e.g., U.S. Pat. No. 4,353,365 to Hallworth et al.) and Handihaler (Boehringer Ingelheim). Further examples of suitable DPI devices are described in U.S. Pat. No. 5,415,162 to Casper et al., U.S. Pat. No. 5,239,993 to Evans, and U.S. Pat. No. 5,715,810 to Armstrong et al., and references cited therein.

In yet another specific embodiment of this invention, the pharmaceutical composition comprising the salt is administered by inhalation using a metered-dose inhaler. Such metered-dose inhalers typically discharge a measured amount of the salt using compressed propellant gas. Accordingly, pharmaceutical compositions administered using a metered-dose inhaler typically comprise a solution or suspension of the salt in a liquefied propellant. Any suitable liquefied propellant may be employed including chlorofluorocarbons, such as $CCl_3F$, and hydrofluoroalkanes (HFAs), such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents, such as ethanol or pentane, and surfactants, such as sorbitan trioleate, oleic acid, lecithin, and glycerin. See, for example, U.S. Pat. No. 5,225,183 to Purewal et al., EP 0717987 A2 to Jinks et al., and WO 92/22286 (Minnesota Mining and Manufacturing Company).

A representative pharmaceutical composition for use in a metered-dose inhaler comprises from about 0.001% to about 5% by weight of a salt of the invention; from about 0% to about 20% by weight ethanol; and from about 0% to about 5% by weight surfactant; with the remainder being an HFA propellant. Another such exemplary pharmaceutical composition comprises from about 0.001% to about 1% by weight of the salt.

Such compositions are typically prepared by adding chilled or pressurized hydrofluoroalkane to a suitable container containing the salt, ethanol (if present) and the surfactant (if present). To prepare a suspension, the salt is micronized and then combined with the propellant and other suitable suspending agents. The formulation is then loaded into an aerosol canister, which forms a portion of a metered-dose inhaler device. Examples of metered-dose inhaler devices developed specifically for use with HFA propellants are provided in U.S. Pat. No. 6,006,745 to Marecki and U.S. Pat. No. 6,143,277 to Ashurst et al. Alternatively, a suspension formulation can be prepared by spray drying a coating of surfactant on micronized particles of the salt. See, for example, WO 99/53901 and WO 00/61108, both to Glaxo Group Ltd.

For additional examples of processes of preparing respirable particles, and formulations and devices suitable for inhalation dosing see U.S. Pat. No. 6,268,533 to Gao et al., U.S. Pat. No. 5,983,956 to Trofast, U.S. Pat. No. 5,874,063 to Briggner et al., and U.S. Pat. No. 6,221,398 to Jakupovic et al.; WO 99/55319 (Glaxo Group Ltd.); and WO 00/30614 (AstraZeneca AB).

In another embodiment, the pharmaceutical compositions of this invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of the salt of this invention.

When intended for oral administration in a solid dosage form (i.e., as capsules, tablets, pills and the like), the pharmaceutical composition will typically comprise a salt of the invention and one or more pharmaceutically acceptable carriers, such as sodium citrate or dicalcium phosphate. Optionally or alternatively, such solid dosage forms may also comprise: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and anti-oxidants can also be present in the pharmaceutical compositions of this invention. Examples of pharmaceutically acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The salt of this invention can also be in micro-encapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Such liquid dosage forms typically comprise a salt of this invention and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuiryl alcohol, polyethylene glycols and fatty acid esters of sorbitan, and mixtures thereof. Suspensions, in addition to the salt, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

When intended for oral administration, the pharmaceutical compositions of this invention are preferably packaged in a unit dosage form. For example, such unit dosage forms may be capsules, tablets, pills, and the like.

The salt of this invention can also be administered transdermally using known transdermal delivery systems and excipients. For example, the salt can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The pharmaceutical compositions of this invention may also contain other therapeutic agents that are co-administered with the salts of this invention. For example, the pharmaceutical composition may further comprise one or more therapeutic agents selected from other bronchodilators (e.g., $PDE_3$ inhibitors, adenosine 2b modulators and $\beta_2$ adrenergic receptor agonists); anti-inflammatory agents (e.g. steroidal anti-inflammatory agents, such as corticosteroids; non-steroidal anti-inflammatory agents (NSAI/Ds), and $PDE_4$ inhibitors); other muscarinic receptor antagonists (i.e., antichlolinergic agents); antiinfective agents (e.g. Gram positive and Gram negative antibiotics or antivirals); antihistamines; protease inhibitors; and afferent blockers (e.g., $D_2$ agonists and neurokinin modulators). In one particular aspect of the invention, a salt of the invention is co-administered with a $\beta_2$ adrenergic receptor agonist and a steroidal anti-inflammatory agent. The other therapeutic agents can be used in the form of pharmaceutically acceptable salts or solvates. Additionally, if appropriate, the other therapeutic agents can be used as optically pure stereoisomers.

Representative $\beta_2$ adrenergic receptor agonists that can be used in combination with a salt of the invention include, but are not limited to, salmeterol, formoterol and arformoterol (R,R-formoterol; Sepracor), salmefamol, fenoterol, albuterol and levalbuterol, metaproterenol, bitolterol, pirbuterol, tolubuterol, broxaterol, terbutaline, isoetharine, and the like, or pharmaceutically acceptable salts thereof. Other $\beta_2$ adrenergic receptor agonists that can be used in combination with the salt of this invention include, but are not limited to: 3-(4-{[6-({(2R)-2-hydroxy-2-[4-hydroxy-3-(hydroxymethyl) phenyl]ethyl}amino)hexyl]oxy}butyl)benzenesulfonamide and 3-(-3-{[7-({(2R)-2-hydroxy-2-[4-hydroxy-3-(hydroxymethyl)phenyl]ethyl}amino)heptyl]oxy}propyl)benzenesulfonamide and related compounds disclosed in WO 02/066422 (Glaxo Group Ltd.); 3-[3-(4-{[6-([(2R)-2-hydroxy-2-[4-hydroxy-3-(hydroxymethyl)phenyl]ethyl}amino)hexyl]oxy}butyl)phenyl]imidazolidine-2,4-dione and related compounds disclosed in WO 02/070490 (Glaxo Group Ltd.); 3-(4-{[6-({(2R)-2-[3-(formylamino)-4-hydroxyphenyl]-2-hydroxyethyl}amino)hexyl]oxy}butyl)benzenesulfonamide, 3-(4-{[6-({(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino)hexyl]oxy}butyl)benzenesulfonamide, N-(tert-butyl)-3-(4-{[6-({(2R)-2-[3-(formylamino)-4-hydroxyphenyl]-2-hydroxyethyl}amino)hexyl]-oxy}butyl)benzenesulfonamide, N-(tert-butyl)-3-(4-{[6-({(2S)-2-[3-(formylamino)-4-hydroxyphenyl]-2-hydroxyethyl}amino)hexyl]oxy}butyl)benzenesulfonamide, N-(tert-butyl)-3-(4-{[6-({(2R/S)-2-[3-(formylamino)-4-hydroxyphenyl]-2-hydroxyethyl}amino)hexyl]oxy}butyl)benzenesulfonamide and related compounds disclosed in WO 02/076933 (Glaxo Group Ltd.); 4-{(1R)-2-[(6-{2-[(2,6-dichlorobenzyl)oxy]ethoxy}hexyl)amino]-1-hydroxyethyl}-2-(hydroxymethyl)phenol and related compounds disclosed in WO 03/024439 (Glaxo Group Ltd.); N-{2-[4-((R)-2-hydroxy-2-phenylethylamino)phenyl]ethyl}-(R)-2-hydroxy-2-(3-formamido-4-hydroxyphenyl)ethylamine and related compounds disclosed in U.S. Pat. No. 6,576,793 to Moran et al.; N-{2-[4-(3-phenyl-4-methoxyphenyl)aminophenyl]ethyl}-(R)-2-hydroxy-2-(8-hydroxy-2(1H)-quinolinon-5-yl)ethylamine and related compounds disclosed in U.S. Pat. No. 6,653,323 to Moran et al.; QAB-149 (Indacaterol; 5-{(1R)-2-[(5,6-diethyl-2,3-dihydro-1H-inden-2-yl)amino]-1-hydroxyethyl}-8-hydroxyquinolin-2 (1H)-one; Novartis Corp.) and similar compounds described in WO 00/75114 and WO 02/45703 (both to Novartis-Erfindungen Verwaltungsgesellschaft M.B.H.; $\beta_2$ adrenergic receptor agonists described in U.S. Patent Publication No. 2004/0229904 (Pfizer Inc.), U.S. Pat. No. 5,019,578 (Merck & Co., Inc.), U.S. Pat. No. 5,030,640 (Merck & Co., Inc.) and WO 2004/071388 (Glaxo Group Ltd.); procaterol (Otsuka Pharmaceutical Co., Ltd.; ML Laboratories); TA-2005 (Tanabe Seiyaku; Chiesi Farmaceutici SpA.); sibenadet hydrochloride (AstraZeneca); S1319 (4-hydroxy-7-[1-(1-hydroxy-2-methylamino)ethyl]-1,3-benzothiazol-2 (3H)-one acetate; Kirin Brewery Co. Ltd.); LAS 32521 (Laboratorios Almirall Prodesfarma, S. A.; WO 96/31466); mabuterol (d,1,-1-(4-amino-3-chloro-5-trifluoromethylphenyl)-2-tert-butylaminoethanol hydrochloride); zilpaterol (Roussel Uclaf; U.S. Pat. No. 4,585,770); meluadrine (CAS No. 134865-33-1); KUR-1246 (Kissei Pharmaceutical); and pharmaceutically acceptable salts thereof. In a particular embodiment, the $\beta_2$ adrenergic receptor agonist is a crystalline monohydrochloride salt of N-{2-[4-((R)-2-hydroxy-2-phenylethylamino)phenyl]ethyl}-(R)-2-hydroxy-2-(3-formamido-4-hydroxyphenyl)ethylamine. When employed, the $\beta_2$ adrenergic receptor agonist will be present in the pharmaceutical composition in a therapeutically effective amount. Typically, the $\beta_2$ adrenergic receptor agonist will be present in an amount sufficient to provide from about 0.05 μg to about 500 μg per dose.

Representative steroidal anti-inflammatory agents that can be used in combination with a salt of the invention include, but are not limited to: methyl prednisolone and prednisolone; dexamethasone; fluticasone propionate; 6α,9α-difluoro-17α-[(2-furanylcarbonyl)oxy]-11β-hydroxy-16α-methyl-3-oxoandrosta-1,4-diene-17β-carbothioic acid S-fluoromethyl ester and similar compounds described in U.S. Pat. No. 6,759,398 to Biggadike (SmithKline Beecham Corporation); 6α,9α-difluoro-11β-hydroxy-16α-methyl-3-oxo-17α-propionyloxyandrosta-1,4-diene-17β-carbothioic acid S-(2-oxotetrahydrofuran-3S-yl)ester and similar compounds described in WO 99/01467 (Glaxo Group Ltd.); beclomethasone esters, for example, the 17-propionate ester or the 17,21-dipropionate ester; budesonide; flunisolide; mometasone esters such as the furoate ester; triamcinolone acetonide; rofleponide; ciclesonide; butixocort propionate; 20R-16α,17α-[butylidenebis(oxy)]-6α,9α-difluoro-11β-hydroxy-17β-(methylthio)androsta-4-en-3-one (RPR-106541; Rhone-Poulenc Rorer Ltd.); ST-126 (SSP/Torii); and the like, or pharmaceutically-acceptable salts thereof. When employed, the steroidal anti-inflammatory agent will be present in the pharmaceutical composition in a therapeutically effective amount. Typically, the steroidal anti-inflammatory agent will be present in an amount sufficient to provide from about 0.05 μg to about 500 μg per dose.

An exemplary combination is a salt of the invention, co-administered with salmeterol as the $\beta_2$ adrenergic receptor agonist, and fluticasone propionate as the steroidal anti-inflammatory agent. Another exemplary combination is a salt of the invention, co-administered with a crystalline monohydrochloride salt of N-{2-[4-((R)-2-hydroxy-2-phenylethylamino)phenyl]ethyl}-(R)-2-hydroxy-2-(3-formamido-4-hydroxyphenyl)ethylamine as the $\beta_2$ adrenergic receptor agonist, and 6α,9α-difluoro-17α-[(2-furanylcarbonyl)oxy]-11β-hydroxy-16α-methyl-3-oxoandrosta-1,4-diene-17β-carbothioic acid S-fluoromethyl ester as the steroidal anti-inflammatory agent.

Representative phosphodiesterase-4 (PDE4) inhibitors or mixed PDE3/PDE4 inhibitors that can be used in combination with a salt of the invention include, but are not limited to: cis 4-cyano-4-(3-cyclopentyloxy-4-methoxyphenyl)cyclohexan-1-carboxylic acid; 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl)cyclohexan-1-ol]; cis-4-cyano-4-[3-(cyclopentyloxy)-4-methoxyphenyl]cyclohexane-1-carboxylic acid and the like, or pharmaceutically acceptable salts thereof. Other representative PDE4 or mixed PDE4/PDE3 inhibitors include: N-(3,5-dichloro-4-pyridinyl)-2-[1-(4-fluorobenzyl)-5-hydroxy-1H-indol-3-yl]-2-oxoacetamide (AWD-12-281; elbion); 9-(2-fluorobenzyl)-N(6)-methyl-2-trifluoromethyladenine (NCS-613; INSERM); 8-methoxyquinoline-5-carboxylic acid (2,5-dichloropyridin-3-yl)amide (D-4418; Chiroscience and Schering-Plough); CI-1018 or PD-168787 (Pfizer Inc.) and N-[9-amino-4-oxo-7-phenyl-1, 2,4,5-tetrahydroazepino[3,2,1-hi]indol-5-yl]nicotinamide (CI-1044 or PD-189659; Pfizer Inc.); benzodioxole compounds disclosed in WO99/16766 (Kyowa Hakko); K-34 (Kyowa Hakko); [3-(3-cyclopentyloxy-4-methoxybenzyl]-8-isopropyl-3H-purin-6-yl]ethylamine hydrochloride (V-11294A; Napp Research Centre Ltd.); roflumilast (Byk-Gulden); pthalazinone compounds disclosed in WO99/47505 (Byk-Gulden); Pumafentrine (Byk-Gulden, now Altana); arofylline (Almirall Prodesfarma, S.A.); VM554/UM565 (Vemalis); 4-[2,3-bis(hydroxymethyl)-6,7-diethoxynaphthyl]-1-(2-hydroxyethyl)hydropyridin-2-one (T-440; Tanabe Seiyaku); and T-2585 and other compounds described in U.S. Pat. No. 6,005,106 to Ukita et al. (Tanabe Seiyaku).

Representative muscarinic antagonists (i.e., anticholinergic agents) that can be used in combination with, and in addition to, a salt of the invention include, but are not limited to: atropine, atropine sulfate, atropine oxide, methylatropine nitrate, homatropine hydrobromide, and anisotropine methyl bromide; hyoscyamine(d,l)hydrobromide; scopolamine hydrobromide; ipratropium bromide, oxitropium bromide, and tiotropium bromide; methantheline; propantheline bromide; clidinium bromide; copyrrolate (Robinul); isopropamide iodide; mepenzolate bromide; tridihexethyl chloride (Pathilone); hexocyclium methylsulfate; cyclopentolate hydrochloride; tropicamide; trihexyphenidyl hydrochloride; pirenzepine; telenzepine; 11-([2-[(diethylamino)methyl]-1-piperdinyl]acetyl)-5,11-dihydro-6H-pyrido[2,3-b][1,4]benzodiazepine-6-one (AF-DX 116); methoctramine; darifenacin; tolterodine; oxybutynin; rispenzepine hydrochloride (CAS No. 96449-05-7; Dompé SpA.); revatropate ((R)-3-quinuclidinyl-(S)-β-hydroxy-α-[2-(R)-methylsulfinyl]ethyl] hydratropate; U.S. Pat. No. 5,543,419 (Pfizer Inc.)); PNU-171990 (2-diisopropylaminoethyl-1-phenylcyclopentane carboxylate hydrochloride; Pfizer Inc.); LAS-34273 and LAS-35201 (Almirall Prodesfarma, S.A.); propiverine hydrochloride (Schering-Plough); trospium chloride (Indevus Pharmaceuticals, Inc.); J-106366 and J-104129 (4-acetamidopiperidine derivatives; Banyu Tsukuba Research Institute and Merck Research Laboratories); and the like; or a pharmaceutically acceptable salt thereof; or, for those compounds listed as a salt, alternate pharmaceutically acceptable salts thereof.

Representative antihistamines (i.e., $H_1$-receptor antagonists) that can be used in combination with the salts of the invention include, but are not limited to: ethanolamines, such as carbinoxamine maleate, clemastine fumarate, diphenylhydramine hydrochloride and dimenhydrinate; ethylenediamines, such as pyrilamine amleate, tripelennamine hydrochloride and tripelennamine citrate; alkylamines, such as chlorpheniramine and acrivastine; piperazines, such as hydroxyzine hydrochloride, hydroxyzine pamoate, cyclizine hydrochloride, cyclizine lactate, meclizine hydrochloride and cetirizine hydrochloride; piperidines, such as astemizole, levocabastine hydrochloride, loratadine or its descarboethoxy analogue, terfenadine and fexofenadine hydrochloride; azelastine hydrochloride; and the like, or a pharmaceutically acceptable salt thereof; or, for those compounds listed as a salt, alternate pharmaceutically acceptable salts thereof.

Other suitable combinations with the salts of the invention include, for example: other anti-inflammatory agents, including NSAIDs (e.g., sodium cromoglycate; nedocromil sodium), FK506 ligands such as pimecrolimus (Elidel; Novartis Pharma AG), and Syk tyrosine kinase inhibitors (R112; Rigel); other phosphodiesterase (PDE) inhibitors such as theophylline; leukotriene antagonists such as monteleukast; inhibitors of leukotriene synthesis; iNOS inhibitors; protease inhibitors, such as tryptase and elastase inhibitors; beta-2 integrin antagonists and adenosine receptor agonists or antagonists, such as adenosine 2a agonists and adenosine 2b antagonists); cytokine antagonists, including chemokine antagonists such as an interleukin antibody (αIL antibody), specifically, an αIL-4 therapy, an αIL-13 therapy, or a combination thereof; and inhibitors of cytokine synthesis.

Suitable doses for the other therapeutic agents administered in combination with a salt of the invention are in the range of about 0.05 μg/day to about 100 mg/day.

The following formulations illustrate representative pharmaceutical compositions of the present invention:

Formulation Example A

A dry powder for administration by inhalation is prepared by the following representative procedure.

| Ingredients | Amount |
| --- | --- |
| Salt of the invention | 0.2 mg |
| Lactose | 25 mg |

The salt is micronized and then blended with lactose. This blended mixture is then loaded into a gelatin or hydroxypropyl methyl cellulose capsule or blister pack. The contents of this unit is then administered using a powder inhaler.

Formulation Example B

A dry powder formulation for use in a dry powder inhalation device is prepared by the following representative procedure. A pharmaceutical composition is prepared having a bulk formulation ratio of a micronized salt of the invention to lactose of 1:200. The composition is packed into a dry powder inhalation device capable of delivering between about 10 μg and about 100 μg of the salt per dose.

Formulation Example C

A dry powder for administration by inhalation in a metered dose inhaler is prepared by the following representative procedure. A suspension containing 5 wt % of a salt of the invention and 0.1 wt % lecithin is prepared by dispersing 10 g of the salt as micronized particles with a mean size of less than 10 μm in a solution formed from 0.2 g of lecithin dissolved in demineralized water (200 mL). The suspension is spray dried and the resulting material is micronized to particles having a mean diameter less than 1.5 μm. The particles are loaded into cartridges with pressurized 1,1,1,2-tetrafluoroethane.

Formulation Example D

A pharmaceutical composition for use in a metered dose inhaler is prepared by the following representative procedure. A suspension containing 5 wt % of a salt of the invention, 0.5 wt % lecithin, and 0.5 wt % trehalose is prepared by dispersing 5 g of active ingredient as micronized particles with mean size less than 10 μm in a colloidal solution formed from 0.5 g of trehalose and 0.5 g of lecithin dissolved in demineralized water (100 mL). The suspension is spray dried and the resulting material is micronized to particles having a mean diameter less than 1.5 μm. The particles are loaded into canisters with pressurized 1,1,1,2-tetrafluoroethane.

Formulation Example E

A pharmaceutical composition for use in a nebulizer inhaler is prepared by the following representative procedure. An inhalation solution for use in a nebulizer is prepared by dissolving 0.1 mg of a salt of the invention in 1 mL of a 0.9% sodium chloride solution containing citric acid as a buffering agent. The mixture is stirred and sonicated until the active ingredient is dissolved. The pH of the solution is adjusted to a value in the range of from 3 to 8 by the slow addition of NaOH. This solution is also suitable as an injectable formulation.

Formulation Example F

Hard gelatin capsules for oral administration are prepared by the following representative procedure:

| Ingredients | Amount |
|---|---|
| Salt of the invention | 250 mg |
| Lactose (spray-dried) | 200 mg |
| Magnesium stearate | 10 mg |

The ingredients are thoroughly blended and then loaded into a hard gelatin capsule (460 mg of composition per capsule).

Formulation Example G

A syrup for oral administration is prepared by the following representative procedure:

| Ingredients | Amount |
|---|---|
| Salt of the invention | 0.5 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Flavoring | 0.035 mL |
| Colorings | 0.5 mg |
| Distilled water | q.s. to 100 mL |

The ingredients are mixed to form a solution containing 50 mg of active ingredient per 10 mL of solution.

Formulation Example H

An injectable formulation is prepared by the following representative procedure:

| Ingredients | Amount |
|---|---|
| Salt of the invention | 0.2 g |
| Sodium acetate buffer solution (0.4 M) | 2.0 mL |
| HCl (0.5 N) or NaOH (0.5 N) | q.s. to pH 4 |
| Water (distilled, sterile) | q.s. to 20 mL |

The above ingredients are blended and the pH is adjusted to 5±0.5 using 0.5 N HCl or 0.5 N NaOH.

Utility

The compound of formula I possesses muscarinic receptor antagonist activity and therefore, a naphthalene-1,5-disulfonic acid salt of this compound is expected to be useful for treating medical conditions mediated by muscarinic receptors, i.e., medical conditions that are ameliorated by treatment with a muscarinic receptor antagonist. Such medical conditions include, by way of example, pulmonary disorders or diseases including those associated with reversible airway obstruction, such as chronic obstructive pulmonary disease (e.g., chronic and wheezy bronchitis and emphysema), asthma, pulmonary fibrosis, allergic rhinitis, rhinorrhea, and the like. Other medical conditions that can be treated with muscarinic receptor antagonists are genitourinary tract disorders, such as overactive bladder or detrusor hyperactivity and their symptoms; gastrointestinal tract disorders, such as irritable bowel syndrome, diverticular disease, achalasia, gastrointestinal hypermotility, disorders and diarrhea; cardiac arrhythmias, such as sinus bradycardia; Parkinson's disease; cognitive disorders, such as Alzheimer's disease; dismenorrhea; and the like.

Accordingly, in one embodiment, this invention is directed to a method for treating a pulmonary disorder, the method comprising administering to a patient in need of treatment a therapeutically effective amount of a naphthalene-1,5-disulfonic acid salt of 2-[(S)-1-(8-methylaminooctyl)pyrrolidin-3-yl]-2,2-diphenylacetamide or a solvate thereof. When used to treat a pulmonary disorder, the salt will typically be administered by inhalation in multiple doses per day, in a single daily dose or a single weekly dose. Generally, the dose for treating a pulmonary disorder will range from about 10 µg/day to about 200 µg/day.

When administered by inhalation, the salts of the invention are expected to provide bronchodilation. Accordingly, in another of its method aspects, this invention is directed to a method of providing bronchodilation in a patient, typically a patient requiring bronchodilation, the method comprising administering a bronchodilation-producing amount of a naphthalene-1,5-disulfonic acid salt of 2-[(S)-1-(8-methylaminooctyl)pyrrolidin-3-yl]-2,2-diphenylacetamide or a solvate thereof. Generally, the dose for providing bronchodilation will range from about 10 µg/day to about 200 µg/day.

In one embodiment, this invention is directed to a method of treating chronic obstructive pulmonary disease or asthma, the method comprising administering to a patient in need of treatment a therapeutically effective amount of a naphthalene-1,5-disulfonic acid salt of 2-[(S)-1-(8-methylaminooctyl)pyrrolidin-3-yl]-2,2-diphenylacetamide or a solvate thereof. When used to treat a COPD or asthma, the salt will typically be administered by inhalation in multiple doses per day or in a single daily dose. Generally, the dose for treating COPD or asthma will range from about 10 µg/day to about 200 µg/day. As used herein, COPD includes chronic obstructive bronchitis and emphysema (see, for example, Barnes, Chronic Obstructive Pulmonary Disease, *N Engl J Med* 2000: 343:269-78).

When used to treat a pulmonary disorder, the salts of this invention are optionally administered in combination with other therapeutic agents. Accordingly, in a particular embodiment, the pharmaceutical compositions and methods of this invention further comprise a therapeutically effective amount of a $\beta_2$ adrenergic receptor agonist, a corticosteroid, a non-steroidal anti-inflammatory agent, or combination thereof.

In another embodiment, the crystalline salts of this invention are used to antagonize a muscarinic receptor in biological system, and a mammal in particular, such as mice, rats, guinea pigs, rabbits, dogs, pigs, humans and so forth. In this embodiment, a muscarinic receptor antagonizing amount of a naphthalene-1,5-disulfonic acid salt of 2-[(S)-1-(8-methylaminooctyl)pyrrolidin-3-yl]-2,2-diphenylacetamide or a solvate thereof, is administered to the mammal. If desired, the effects of antagonizing the muscarinic receptor can then determined using conventional procedures and equipment.

The properties and utility of the naphthalene-1,5-disulfonic acid salts of this invention can be demonstrated using various in vitro and in vivo assays well-known to those skilled in the art. For example, representative assays are described in further detail in the following Examples.

EXAMPLES

The following Preparations and Examples are provided to illustrate specific embodiments of this invention. These specific embodiments, however, are not intended to limit the scope of this invention in any way unless specifically indicated.

The following abbreviations have the following meanings unless otherwise indicated and any other abbreviations used herein and not defined have their standard meaning:

AC adenylyl cyclase
Ach acetylcholine
ACN acetonitrile
BSA bovine serum albumin
cAMP 3'-5' cyclic adenosine monophosphate
CHO Chinese hamster ovary
$cM_5$ cloned chimpanzee $M_5$ receptor
DABCO 1,4-diazabicyclo[2.2.2]octane
DCM dichloromethane (i.e., methylene chloride)
DIPEA N,N-diisopropylethylamine
dPBS Dulbecco's phosphate buffered saline
DMSO dimethyl sulfoxide
EDTA ethylenediaminetetraacetic acid
EtOAc ethyl acetate
EtOH ethanol
FBS fetal bovine serum
FLIPR fluorometric imaging plate reader
HBSS Hank's buffered salt solution
HEPES 4-(2-hydroxyethyl)-1-piperazineethanesulfonic acid
$hM_1$ cloned human $M_1$ receptor
$hM_2$ cloned human $M_2$ receptor
$hM_3$ cloned human $M_3$ receptor
$hM_4$ cloned human $M_4$ receptor
$hM_5$ cloned human $M_5$ receptor
HPLC high-performance liquid chromatography
iPrAc isopropyl acetate
MeOH methanol
MTBE methyl tert-butyl ether
RH relative humidity
TFA trifluoroacetic acid
THF tetrahydrofuran Unless noted otherwise, reagents, starting materials and solvents were purchased from commercial suppliers (such as Aldrich, Fluka, Sigma and the like) and were used without further purification.

In the examples described below, HPLC analysis was conducted using an Agilent (Palo Alto, Calif.) Series 1100 instrument with Zorbax Bonus RP 2.1×50 mm columns, supplied by Agilent, (a C14 column), having a 3.5 micron particle size. Detection was by UV absorbance at 214 nm. HPLC 10-70 data was obtained with a flow rate of 0.5 mL/minute of 10%-70% B over 6 minutes. Mobile phase A was 2%/98%/0.1% ACN/$H_2$O/TFA; and mobile phase B was 90%/10%/0.1% ACN/$H_2$O/TFA. Using the mobile phases A and B described above, HPLC 5-35 data and HPLC 10-90 data were obtained with a 5 minute gradient.

Liquid chromatography mass spectrometry (LC/MS) data were obtained with an Applied Biosystems (Foster City, Calif.) model API-150EX instrument. LC/MS 10-90 data was obtained with a 10%-90% mobile phase B over a 5 minute gradient.

Small scale purification was conducted using an API 150EX Prep Workstation system from Applied Biosystems. Mobile phase A was water+0.05% v/v TFA, and mobile phase B was ACN+0.05% v/v TFA. For arrays (typically about 3 to 50 mg recovered sample size) the following conditions were used: 20 mL/min flow rate; 15 min gradients and a 20 mm×50 mm Prism RP column with 5 µm particles (Thermo Hypersil-Keystone, Bellefonte, Pa.). For larger scale purifications (typically greater than 100 mg crude sample), the following conditions were used: 60 mL/min flow rate; 30 min gradients and a 41.4 mm×250 mm Microsorb BDS column with 10 micron particles (Varian, Palo Alto, Calif.).

The specific rotation for chiral compounds (indicated as $[\alpha]^{20}_D$) was measured using a Jasco Polarimeter (Model P-1010) with a tungsten halogen light source and a 589 nm filter at 20° C. Samples of test compounds were typically measured at 1 mg/mL water.

Preparation 1

(S)-1-Benzyl-3-(p-toluenesulfonyloxy)pyrrolidine

To a stirred solution of (S)-1-benzyl-3-pyrrolidinol (44.3 g, 0.25 mol) and DABCO (33.7 g, 0.3 mol) in MTBE (250 mL) under an atmosphere of nitrogen at 0° C., was added p-toluenesulfonyl chloride (52.4 g, 0.275 mol) portionwise over 20 minutes. The reaction mixture was stirred at 0° C. for 1 hour. The ice bath was removed and the mixture was stirred at ambient temperature overnight (20±5 hours). EtOAc (100 mL) was added, followed by saturated aqueous sodium bicarbonate solution (250 mL). The resulting mixture was stirred at ambient temperature for 1 hour. The layers were separated and the organic layer was washed with saturated aqueous sodium bicarbonate solution (250 mL); saturated aqueous ammonium chloride solution (250 mL); saturated aqueous NaCl solution (250 mL); and then dried over sodium sulfate (80 g). The sodium sulfate was filtered off and washed with EtOAc (20 mL) and the solvent was removed in vacuo to give 78.2 g of the title intermediate as an off-white solid (94% yield; 95% purity by HPLC).

Preparation 2

(S)-1-Benzyl-3-(1-cyano-1,1-diphenylmethyl)pyrrolidine

To a stirred solution of diphenylacetonitrile (12.18 g, 61.8 mmol) in anhydrous THF (120 mL) at 0° C., potassium tert-butoxide (10.60 g, 94.6 mmol) was added over 5 minutes. The reaction mixture was stirred at 0° C. for 1 hour. To the reaction mixture at 0° C. was added (S)-1-benzyl-3-(p-toluenesulfonyloxy)pyrrolidine (20.48 g, 61.3 mmol) in one portion. The cold bath was removed and the reaction mixture was stirred for 5-10 minutes at which time the reaction mixture had become a brown homogeneous solution. The reaction mixture was then heated at 40° C. overnight (20±5 hours). The reaction mixture (bright yellow suspension) was allowed to cool to room temperature before adding water (150 mL). Most of the THF was then removed in vacuo and isopropyl acetate (200 mL) was added. The layers were separated and the organic layer was washed with saturated aqueous ammonium chloride solution (150 mL); saturated aqueous sodium chloride solution (150 mL); and then dried over sodium sulfate (50 g). The sodium sulfate was filtered off and washed with isopropyl acetate (20 mL) and the solvent was removed in vacuo to give 23.88 g of the title intermediate as a light brown oil (>99% yield, 75% purity by HPLC, contaminated mainly with excess diphenylacetonitrile).

Preparation 3

(S)-3-(1-Cyano-1,1-diphenylmethyl)pyrrolidine (S)-1-Benzyl-3-(1-cyano-1,1-diphenylmethyl)pyrrolidine was dissolved in iPrAc (approximately 1 g/10 mL) and the solution was mixed with an equal volume of 1N aqueous HCl. The resulting layers were separated and the aqueous layer was extracted with an equal volume of iPrAc. The organic layers were combined, dried over sodium sulfate and filtered. The solvent was removed in vacuo to afford (S)-1-benzyl-3-(1-cyano-1,1-diphenylmethyl)pyrrolidine hydrochloride as a light yellow foamy solid. (Note: This hydrochloride salt can also be prepared during the work-up of Preparation 2).

To a stirred solution of (S)-1-benzyl-3-(1-cyano-1,1-diphenylmethyl)pyrrolidine hydrochloride (8.55 g, 21.98 mmol) in MeOH (44 mL) was added palladium on carbon (1.71 g) and ammonium formate (6.93 g, 109.9 mmol). The reaction mixture was heated to 50° C. with stirring for 3 hours. The reaction was cooled to ambient temperature and water (20 mL) was added. The resulting mixture was filtered through a pad of Celite, washing with MeOH (20 mL). The filtrate was collected and most of the MeOH was removed in vacuo. The residue was mixed with iPrAc (100 mL) and 10% aqueous sodium carbonate (50 mL). The resulting layers were separated and the aqueous layer was extracted with iPrAc (50 mL). The organic layers were combined and dried over sodium sulfate (20 g). The sodium sulfate was filtered off and washed with iPrAc (20 mL). The solvent was removed in vacuo to afford 5.75 g of the title intermediate as a light yellow oil (99.7% yield, 71% purity by HPLC).

Preparation 4

2,2-Diphenyl-2-(S)-pyrrolidin-3-ylacetamide

A 200 mL flask with a magnetic stir bar and a nitrogen inlet was charged with (S)-3-(1-cyano-1,1-diphenylmethyl)pyrrolidine (2.51 g) and 80% $H_2SO_4$ (19.2 mL; pre-prepared with 16 mL of 96% $H_2SO_4$ and 3.2 mL of $H_2O$). The reaction mixture was then heated at 90° C. for 24 hours or until the starting material was consumed as indicated by HPLC. The reaction mixture was allowed to cool to room temperature and then poured onto ice (approximately 50 mL by volume). A 50% aqueous NaOH solution was added slowly to the mixture with stirring over an ice bath until the pH was about 12. DCM (200 mL) was added and mixed with the aqueous solution at which time sodium sulfate precipitated out and was filtered off. The filtrate was collected and the layers were separated. The aqueous layer was extracted with DCM (100 mL) and the organic layers were combined and dried with over sodium sulfate (5 g). The sodium sulfate was filtered off and washed with DCM (10 mL). The solvent was removed in vacuo to give the crude product as a light yellow foamy solid (approximately 2.2 g, 86% purity by HPLC).

The crude product was dissolved in EtOH (18 mL) with stirring. To this solution was added a warm solution of L-tartaric acid (1.8 g) in EtOH (14 mL) and the resulting mixture was stirred overnight (15±5 hours). The resulting precipitate was isolated by filtration to give an off-white solid (approximately 3.2 g, >95% purity by HPLC). MeOH (15 mL) was added to this solid and the resulting slurry was stirred at 70° C. overnight (15 hours). The slurry was allowed to cool to ambient temperature and a white solid (~2.6 g, >99% purity by HPLC) was obtained after filtration. To this solid was added EtOAc (30 mL) and 1 N aqueous NaOH (25 mL). This mixture was mixed until two distinct layers formed and then the layers were separated and the aqueous layer was extracted with EtOAc (20 mL). The organic layers were combined and dried over sodium sulfate (10 g). The sodium sulfate was removed by filtration and the solvent was evaporated in vacuo to afford 1.55 g of the title intermediate as an off-white foamy solid (58% yield; >99% purity by HPLC).

Preparation 5

8-(N-Benzyl-N-methylamino)octan-1-ol

8-Bromo-1-octanol (25 g, 119.6 mmol) in ACN (50 mL) was added to a stirred solution of N-benzyl-N-methylamine (43.49 g, 358.9 mmol) and potassium carbonate (49.52 g, 358.9 mmol) in ACN (250 mL) at 35° C. The reaction mixture was then stirred at 35° C. for 7 hours and then cooled to ambient temperature. The potassium carbonate was filtered and the filtrate was concentrated under reduced pressure. The crude residue was dissolved in MTBE (400 mL) and the organic phase was washed with water, brine and dried over magnesium sulfate. N-methyl-2-pyrrolidone was added and the mixture was concentrated under reduced pressure to remove excess N-benzyl-N-methylamine. MTBE (400 mL) was added and the organic phase was washed with water, brine, and dried over magnesium sulfate, filtered and concentrated under reduced pressure to afford the title intermediate as an oil (~100% conversion). MS m/z 250.3 (MH$^+$).

Preparation 6

8-(N-Benzyl-N-methylamino)octanal

DMSO (22.71 mL, 320 mmol) and then DIPEA (55.74 mL, 320 mmol) were added to a stirred solution of the intermediate from Preparation 5 (20 g, 80 mmol) in DCM (200 mL) at −10° C. The reaction mixture was stirred at −10° C. for 30 minutes, then sulfur trioxide pyridine complex (38 g, 240 mmol) was added portionwise. The reaction mixture was stirred for an additional 1 hour at −10° C. and then water (200 mL) was added. The organic layer was separated and washed with water (200 mL), brine (30 mL), dried over magnesium sulfate and then concentrated under reduced pressure. Toluene (100 mL) was added and removed under reduced pressure to afford the title intermediate as oil (~100% conversion).

Preparation 7

2-[(S)-1-(8-N-Benzyl-N-methylaminooctyl)pyrrolidin-3-yl]-2,2-diphenylacetamide

A solution of the intermediate from Preparation 6 (5.95 g, 24 mmol) and 2,2-diphenyl-2-(S)-pyrrolidin-3-ylacetamide (7.4 g, 26.4 mmol) in DCM (250 mL) was cooled at 0° C. and stirred for 10 minutes. Sodium triacetoxyborohydride (8.4 g, 36 mmol) was added portionwise at 0° C. and the reaction mixture was stirred at room temperature for 4 hours. DCM was added and the organic phase was washed with sodium bicarbonate (2×), brine (1×), dried over magnesium sulfate and concentrated under reduced pressure. The crude product was purified by flash chromatography (DCM/MeOH/NH$_4$OH=90/9/1) to give 9 g of the title intermediate as an oil (75% yield). MS m/z 512.8 (MH$^+$).

Example 1

2-[(S)-1-(8-Methylaminooctyl)pyrrolidin-3-yl]-2,2-diphenylacetamide

To a stirred solution of the intermediate from Preparation 7 (9 g, 17.6 mmol) in acetic acid (170 mL) under a nitrogen atmosphere was added palladium on carbon (10 wt %, 600 mg) and palladium hydroxide on carbon (20 wt %, wet, 600 mg). The reaction mixture was flushed with nitrogen three times and then placed under a hydrogen-containing balloon for 3 days at room temperature. The reaction mixture was filtered through Celite, washing with acetic acid, and the solvent was removed under reduced pressure. The resulting residue was purified by prep HPLC to afford the title compound as its bis-trifluoroacetic acid salt, which was an oil (4.02 g, 35% yield). MS m/z 422.2 (MH$^+$).

Preparation 8

8-(N-Benzyl-N-methylamino)octan-1-ol

To a 250 mL flask was charged N-benzyl-N-methylamine (24.3 g, 200 mmol), potassium carbonate (28 g, 200 mmol), 8-bromooctan-1-ol (14 g, 67 mmol) and ACN (150 mL). This reaction mixture was stirred at 35° C. to 40° C. for 5 hours. The solid material was then filtered and the filtrate was distilled to an oil under high vacuum to remove excess N-benzyl-N-methylamine. The residue was dissolved in MTBE (150 mL) and washed with 15% ammonium chloride solution (2×100 mL), brine (100 mL), dried with 20 g of sodium sulfate, filtered and distilled under vacuum to give the title intermediate as an oil (13.2 g, 79% yield).

Preparation 9

Toluenesulfonic Acid 8-(N-Benzyl-N-methylamino)octan-1-yl Ester

A 250 mL flask was charged with the intermediate from Preparation 8 (10 g), DABCO (6.72 g), and MTBE (100 ml). The reaction mixture was cooled to <10° C. and a solution of toluenesulfonic chloride (9.2 g) in MTBE (60 mL) was added at <15° C. This reaction mixture was stirred at room temperature for 2 h and then heptane (40 mL) was added and the mixture was filtered. The filtrate was distilled under vacuum to give the title intermediate as an oil (16 g, 99% yield).

Preparation 10

2-[(S)-1-(8-N-Benzyl-N-methylaminooctyl)pyrrolidin-3-yl]-2,2-diphenylacetamide

A 1000 mL flask with a nitrogen inlet was charged with the intermediate from Preparation 9 (16 g), 2,2-diphenyl-2-(S)-pyrrolidin-3-ylacetamide (10 g), DIPEA (10.3 g) and ACN (200 mL). The reaction mixture was stirred at 45° C. to 50° C. for 20 hours and then acetic anhydride (2 g) was added and the mixture stirred at room temperature for 2 hours. MTBE (300 mL) and water (400 mL) were added and the MTBE layer was separated and washed with water (2×150 mL) and then 1N HCl (1×150 mL). The aqueous layer was separated and washed with MTBE (3×100 mL) and then made basic with 27% ammonium hydroxide solution to pH >12. The basic aqueous layer was then extracted with MTBE (2×200 mL) and the MTBE layer was washed with water (200 mL), brine (200 mL), dried over sodium sulfate (20 g), filtered and distilled to give the title intermediate as an oil (16.5 g, 90% yield). If desired, this reaction can be conducted in N-methylpyrrolidone as the solvent. Additionally, potassium carbonate or sodium carbonate can be used in place of diisopropylethylamine and optionally sodium iodide may be added to the reaction mixture.

Example 2

2-[(S)-1-(8-Methylaminooctyl)pyrrolidin-3-yl]-2,2-diphenylacetamide

A 250 mL flask was charged with the intermediate from Preparation 10 (24 g), palladium on carbon (10% palladium on carbon with 50% water, 5.3 g), isopropanol (160 mL) and 3 M HCl solution (30 mL). The reaction mixture was degassed with nitrogen and then was hydrogenated (45-50 psi) at room temperature for 16 hours. The mixture was then filtered though a Celite pad and the filtrate was distilled to a volume of about 50 mL. The residue was dissolved in 1 N HCl (100 mL) and washed with DCM (2×100 mL). The aqueous layer was adjusted to pH >12 by adding ammonium hydroxide and then extracted using MTBE (2×150 mL). The MTBE solution was then washed with water (100 mL), brine (100 mL), dried over sodium sulfate (30 g), filtered and the solvent reduced to give an oil which was dried under high vacuum to give the title compound (16.5 g, 91% yield).

Preparation 11

8,8-Dimethoxyoctanal

A 1 L flask was charged with cyclooctene (50 g), MeOH (250 mL) and DCM (250 mL). Ozone was bubbled into the solution at −70° C. for 8 hours. Toluenesulfonic acid (3 g) was then added and the reaction mixture was stirred at −70° C. for 6 hours. Sodium bicarbonate (20 g) was then added and the reaction mixture was stirred for an additional 2 hours at −60° C. Finally, dimethyl sulfite (56 g) was added at −60° C. and the reaction mixture was stirred at room temperature for 16 hours. The solid that had formed was filtered and filtrate was evaporated to oil. The oil was dissolved in DCM (300 mL) and washed with 1% sodium bicarbonate solution (2×150 mL). The DCM solution was then dried over sodium sulfate (50 g), filtered and distilled to give the title intermediate as an oil (60.3 g, 71% yield).

Preparation 12

2-[(S)-1-(8-Oxooctyl)pyrrolidin-3-yl]-2,2-diphenylacetamide

A 100 mL flask was charged with 2,2-diphenyl-2-(S)-pyrrolidin-3-ylacetamide (2.8 g), 8,8-dimethoxyoctanal (2.1 g), and DCM (20 mL) and this mixture was stirred at room temperature for 1 hour. Sodium triacetoxyborohydride (3.18 g) was added and the reaction mixture was stirred at room temperature for 14 hours. A solution of 5% sodium bicarbonate (350 mL) was then added and this mixture stirred for 0.5 hours. The layers were separated and the aqueous layer was extracted with DCM (20 mL). The combined DCM solution was concentrated to a volume of about 20 mL, filtered through a silica gel pad (10 g) and washed with 10% MeOH in DCM (100 mL). The product solution was concentrated to an oil and the oil was dissolved in ACN (50 mL) and stirred with 1% HCl (30 mL) for 16 hours. The mixture was made basic to approximately pH >12 by adding 28% ammonium hydroxide solution and then extracted with MTBE (2×100 mL). The MTBE layer was washed with brine (100 mL), dried over sodium sulfate (10 g), filtered and concentrated under vacuum to give the title intermediate as an oil (3.8 g, 93% yield).

Preparation 13

2-[(S)-1-(8-N-Benzyl-N-methylaminooctyl)pyrrolidin-3-yl]-2,2-diphenylacetamide

A 100 mL flask with a nitrogen inlet was charged with the intermediate from Preparation 12 (3 g), N-benzyl-N-methylamine (2.1 g) and DCM (20 mL) and this mixture was stirred at room temperature for 1 hour. Sodium triacetoxyborohydride (3.18 g) was added and the reaction mixture was stirred at room temperature for 14 hours. The reaction was then quenched by adding 5% HCl (50 mL) and the resulting mixture was stirred for 0.5 hours. The layers were separated and the aqueous layer was washed with DCM (20 mL). The aqueous layer was adjusted to pH >13 by adding 50% potassium hydroxide and extracted with MTBE (2×100 mL). The combined MTBE solution was washed with brine (100 mL), dried with sodium sulfate (10 g), filtered and concentrated to give the title intermediate as an oil (2.8 g, 75% yield). Using the procedure described in Example 2, this intermediate was converted into 2-[(S)-1-(8-methylaminooctyl)pyrrolidin-3-yl]-2,2-diphenylacetamide.

Example 3

2-[(S)-1-(8-Methylaminooctyl)pyrrolidin-3-yl]-2,2-diphenylacetamide Naphthalene-1,5-disulfonic Acid Salt 2-[(S)-1-(8-Methylaminooctyl)pyrrolidin-3-yl]-2,2-diphenylacetamide (0.084 g, 0.2 mmol, free base) was dissolved in isopropanol (2 mL). A solution of naphthalene-1,5-disulfonic acid (0.058 g, 0.2 mmol) in a mixture of EtOH (1.7 mL) and water (0.3 mL) was added slowly and the reaction mixture was heated at 45° C. to 50° C. for about 20 minutes. The reaction mixture was then cooled slowly to room temperature at which time the solution became cloudy and then formed a white suspension. This mixture was allowed to sit overnight at ambient temperature (under a gentle stream of nitrogen). The resulting crystals were then collected by filtration and then dried to give the title compound (0.92 g, 65% yield) as a white crystalline solid.

Figure 5:
FIG. 5 is a micrographic image of a crystalline naphthalene-1,5-disulfonic acid salt of 2-[(S)-1-(8-methylaminooctyl)pyrrolidin-3-yl]-2,2-diphenylacetamide.

When examined under a microscope using polarized light, the crystals exhibited birefringence and appeared to have plate/granular morphology, as illustrated in the micrographic image of FIG. 5.

Preparation 14

8-(Benzylmethylamino)octan-1-ol

A 2-L flask was charged with benzylmethylamine (270 g, 2.23 mol), sodium carbonate (157 g, 1.48 mol), sodium iodide (11.1 g, 0.074 mol), 8-chlorooctanol (122 g, 0.74 mol) and ACN (1000 mL) and the resulting suspension was stirred at 80° C. for 20-30 hours. The reaction mixture was then concentrated to a volume of about 500 mL and water (600 mL) and MTBE (1000 mL) were added. The MTBE layer was then separated and washed with water (500 mL). The MTBE solution was concentrated under vacuum and the resulting oil was then further concentrated by distillation under high vacuum to remove excess benzylmethylamine. N-methyl-2-pyrrolidone (300 mL) was then added to the remaining oil and this solution concentrated by distillation under high vacuum to provide an oil. The oil was dissolved in MTBE (1000 mL) and the resulting solution was washed with water (2×500 mL), brine (500 mL), dried with sodium sulfate (100 g), filtered and concentrated by distillation to afford the title compound as an oil (178 g, 96% yield, >95% purity).

Preparation 15

8-(N-tert-Butoxycarbonyl-N-methylamino)octan-1-ol

A 1-L flask was charged with the product of Preparation 14 (49 g, 0.20 mol), isopropanol (400 mL), 2 N aqueous HCl (100 mL) and activated carbon (5 g, DARCO) and the resulting mixture was stirred for 30 minutes. The mixture was then filtered to remove the activated carbon and to the filtrate was added palladium on carbon (5 g, 10% dry weight). The resulting mixture was degassed three times with nitrogen and then twice with hydrogen; and then the mixture was hydrogenated on a Parr shaker at 20-30 psi hydrogen for 12-24 hours. The mixture was then filtered through a 20 g pad of Celite and concentrated by distillation to a volume of about 100 mL. Isopropanol (200 mL) was added and this solution was again concentrated by distillation under vacuum to a volume of about 100 mL. This procedure was repeated two more times to give a solution containing 8-methylaminooctan-1-ol hydrochloride.

A 1-L flask was charged with the 8-methylaminooctanol hydrochloride isopropanol solution from above and triethylamine (30.3 g, 0.30 mol), and to this mixture was added di-tert-butyl dicarbonate (48 g, 0.22 mol) in portions. The resulting mixture was stirred at room temperature for 2-5 hours and then the mixture was concentrated to a volume of about 300 mL. Water (200 mL) and EtOAc (400 mL) were added and this mixture was stirred for 15 minutes. The organic layer was then separated and washed with water (300 mL), brine (300 mL), dried over $Na_2SO_4$ (50 g), filtered and solvent reduced under vacuum to afford the title compound as a light yellow oil. (40 g, 77% yield, ~95% purity).

Preparation 16

Toluene-4-sulfonic Acid
8-(N-tert-Butoxycarbonyl-N-methylamino)octyl
Ester

In a 250 mL flask, a solution of the product from Preparation 15 (5.2 g, 20 mmol) and DABCO (3.13 g, 2.8 mmol) in MTBE (30 mL) was cooled to about 10° C. and a solution of p-toluenesulfonyl chloride (4.2 g, 22 mmol) in MTBE (20 mL) was added while maintaining the temperature of the reaction mixture at 20° C. or less. The resulting solution was then stirred at room temperature for 2 hours. Water (100 mL) was added and the mixture was stirred for 15 minutes. The organic layer was separated, washed with water (100 mL), brine (100 mL) and then concentrated by distillation to give the title compound as an oil.

Preparation 17

2-{(S)-1-[8-(N-tert-Butoxycarbonyl-N-methylamino)octyl]pyrrolidin-3-yl}-2,2-diphenylacetamide To a 500 mL flask was added the product from Preparation 16 (17.68 g, 43 mmol), the product from Preparation 1 (12 g, 43 mmol), DIPEA (16.55 g, 128 mmol) and ACN (100 mL). The resulting mixture was stirred at 60° C. to 65° C. for 5 to 7 hours and then cooled to room temperature. The solvent was reduced in vacuo and iPrAc (100 mL) was added to dissolve the residue. The resulting solution was washed with water (100 mL), saturated $NaHCO_3$ solution (100 mL), brine (100 mL), dried over $MgSO_4$ (5 g) and filtered to afford an orange solution.

A silica gel (115 g, 280-400 mesh) pad was pre-treated with iPrAc (400 mL) containing 1% triethylamine, following by iPrAc (250 mL) (the silica gel pad is about 6.4 cm in diameter and about 10.2 cm in height). The filtrate from above (about 150 mL in volume) was loaded directly onto the pre-treated silica pad and eluted with iPrAc (400 mL) and then with 20% isopropanol in iPrAc (1000 mL). The product fractions were combined and concentrated to afford the title compound as an oil (17.16 g, 77% yield, 97% purity).

Example 4

2-[(S)-1-(8-Methylaminooctyl)pyrrolidin-3-yl]-2,2-diphenylacetamide Naphthalene-1,5-disulfonic Acid Salt To a 1000 mL flask was added the product from Preparation 17 (9.88 g, 19 mmol), 1,5-naphthalenedisulfonic acid tetrahydrate (13.69 g, 38 mmol, ≧97% purity by HPLC) and isopropanol containing 3% water (497 mL). This mixture was heated to 85° C. for 3 to 5 hours, then slowly cooled to room temperature over a 4 hour period and then stirred at room temperature for 12 to 24 hours. The resulting solid was filtered and washed with isopropanol containing 3% water by volume (400 mL) and dried under vacuum for 10 to 15 hours at room temperature to give the title compound as a crystalline solid (12.59 g, 95% yield, ~99% purity).

Example 5

Purification of 2-[(S)-1-(8-Methylaminooctyl)pyrrolidin-3-yl]-2,2-diphenylacetamide Naphthalene-1,5-disulfonic Acid Salt To a 1 L flask was added 2-[(S)-1-(8-methylaminooctyl)pyrrolidin-3-yl]-2,2-diphenylacetamide naphthalene-1,5-disulfonic acid salt (21.4 g, 30.1 mmol) and isopropanol containing 3% water by volume (637 mL). The resulting slurry was stirred at 80° C. for 2 hours and then slowly cooled to room temperature and then stirred at room temperature for 12 hours. The resulting crystalline salt was filtered, washed with isopropanol (600 mL) and then dried under vacuum and nitrogen for 16 hours at room temperature to give the title compound as a white, crystalline solid (20.4 g, 96% yield).

Example 6

Powder X-Ray Diffraction

Powder x-ray diffraction patterns were obtained with a Thermo ARL X-Ray Diffractometer Model X'TRA (Thermo ARL SA, Switzerland) using Cu Kα radiation at 1.542 Å (45 kV, 40 mA) with a Si(Li) solid-state detector. The analysis was typically performed at a scan rate of 2°/min with a step size of 0.03° per point over a range of 2 to 30° in two-theta angle. Samples, either as received or ground to a fine powder, were gently packed into a custom small-volume insert designed to fit into the instrument top-loading sample cup for analysis. The instrument was calibrated weekly to a silicon metal standard, within ±0.02° two-theta angle. A representative PXRD pattern for a sample of the crystalline naphthalene-1,5-disulfonic acid salt of 2-[(S)-1-(8-methylaminooctyl)pyrrolidin-3-yl]-2,2-diphenylacetamide of Example 5 is shown in FIG. 1.

Example 7

Thermal Analysis

Differential scanning calorimetry (DSC) was performed using a TA Instruments Model Q-10 module with a Thermal Analyst controller. Data were collected and analyzed using TA Instruments Thermal Solutions software. A sample of about 1 mg was accurately weighed into an aluminum pan with lid. The sample was evaluated using a linear heating ramp of 5° C./min from ambient temperature to approximately 300° C. The DSC cell was purged with dry nitrogen during use. A representative DSC trace for a sample of the crystalline naphthalene-1,5-disulfonic acid salt of 2-[(S)-1-(8-methylaminooctyl)pyrrolidin-3-yl]-2,2-diphenylacetamide of Example 5 is shown in FIG. 2.

Thermogravimetric analysis (TGA) was performed using a TA Instruments Model Q-50 module equipped with high resolution capability. Data were collected and analyzed using TA Instruments Thermal Solutions software. A sample weighing about 10 mg was placed onto a platinum pan and scanned with a high resolution-heating rate from ambient temperature to 300° C. The balance and furnace chambers were purged with nitrogen flows during use. A representative TGA trace for a sample of the crystalline naphthalene-1,5-disulfonic acid salt of 2-[(S)-1-(8-methylaminooctyl)pyrrolidin-3-yl]-2,2-diphenylacetamide of Example 5 is shown in FIG. 2.

The DSC trace demonstrates that a naphthalene-1,5-disulfonic acid salt of the present invention has excellent thermal stability with the melting peak at about 211° C. and no thermal decomposition below 200° C. The DSC trace shows an onset of endothermic heat flow at about 200° C. The TGA trace indicates that the naphthalene-1,5-disulfonic acid salt of the present invention lost a small amount (about 0.5%) of weight from room temperature to 120° C., which is consistent with the loss of residual moisture or solvent.

Example 8

Dynamic Moisture Sorption Assessment

Figure 3:
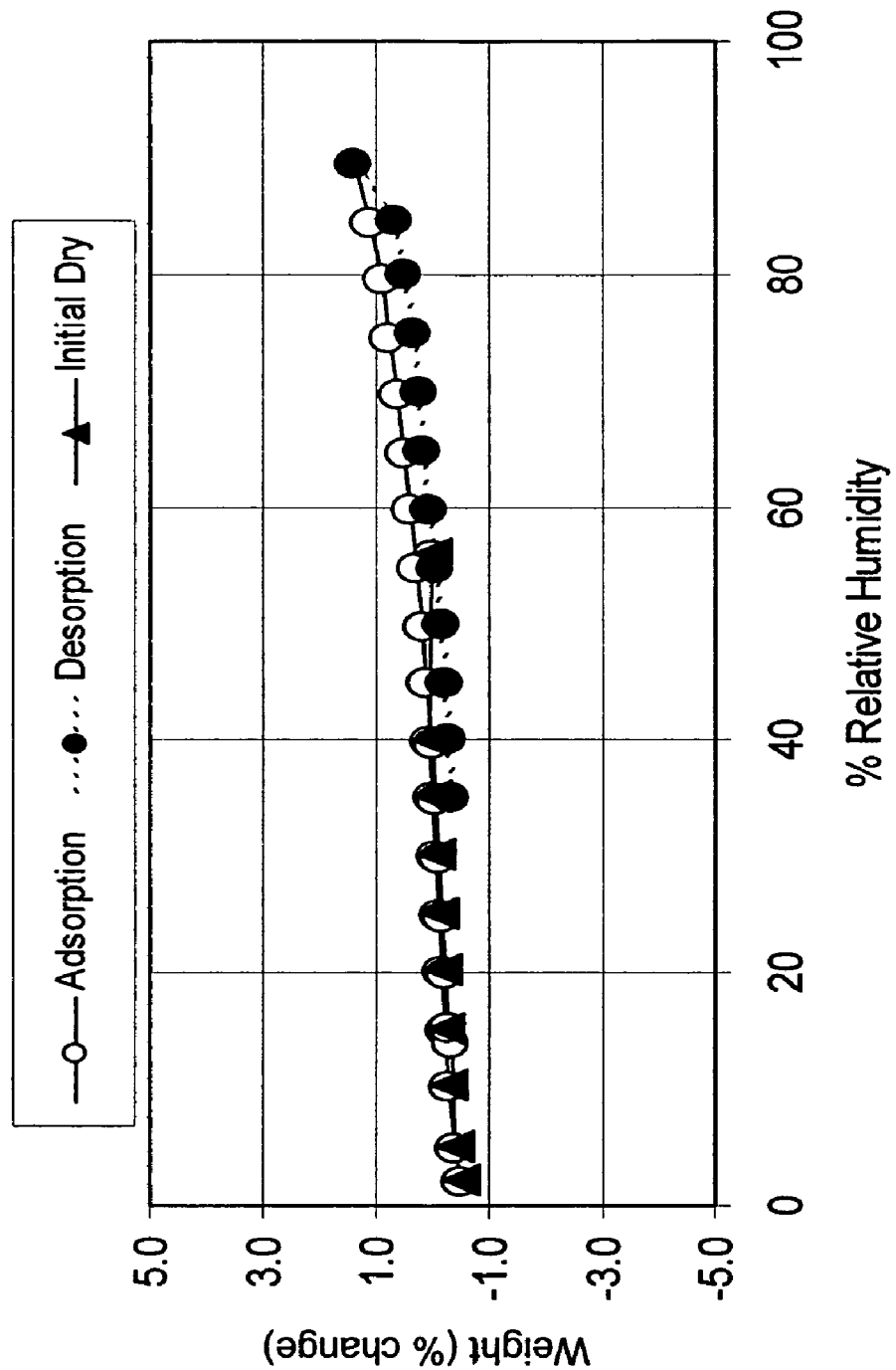
FIG. 3 shows a dynamic moisture sorption (DMS) trace for a crystalline naphthalene-1,5-disulfonic acid salt of 2-[(S)-1-(8-methylaminooctyl)pyrrolidin-3-yl]-2,2-diphenylacetamide.

A dynamic moisture sorption (DMS) assessment (also known as a moisture sorption-desorption profile) was performed for a sample of a crystalline naphthalene-1,5-disulfonic acid salt of 2-[(S)-1-(8-methylaminooctyl)pyrrolidin-3-yl]-2,2-diphenylacetamide (prepared according to the procedure of Example 5) using a VTI atmospheric microbalance, SGA-100 system (VTI Corp., Hialeah, Fla. 33016). A sample size of approximately 10 mg was used and the humidity was set at the ambient value at the start of the analysis. A typical DMS analysis consisted of three scans: ambient to 2% RH, 2% RH to 90% RH, 90% RH to 5% RH at a scan rate of 5% RH/step. The mass was measured every two minutes and the RH was changed to the next value (+/−5% RH) when the mass of the sample was stable to within 0.01% for 5 consecutive points. A representative DMS trace is shown in FIG. 3.

The DMS trace demonstrates that a naphthalene-1,5-disulfonic acid salt of the present invention has a reversible sorption/desorption profile with moderate (<5%) hygroscopicity. The salt has an acceptable 1.9% weight gain when it exposed to a broad humidity range from 2% RH up to 90% RH and it has a less than 1% weight gain in the humidity range of 40% RH to 75% RH. The reversible moisture sorption/desorption profile demonstrates that a crystalline salt of the present invention possesses an acceptable hygroscopicity and is not deliquescent.

Example 9

Infrared Analysis

The infrared (IR) absorption spectrum was determined over the frequency range 4000 to 675 cm$^{-1}$ using an Avatar 360 FT-IR spectrometer equipped with a Nicolet attenuated total reflection (ATR) sample holder. A representative IR absorption spectrum for a sample of a crystalline naphthalene-1,5-disulfonic acid salt of 2-[(S)-1-(8-methylaminooctyl)pyrrolidin-3-yl]-2,2-diphenylacetamide (prepared according to the procedure of Examples 4 and 5) had significant absorption bands at 696±1, 704±1, 765±1, 800±1, 1028±1, 1154±1, 1172±1, 1191±1, 1217±1, 1230±1, 1245±1, and 1669±1 cm$^{-1}$, as illustrated in FIG. 4.

Example 10

Solid State Stability Assessment

Samples of the crystalline naphthalene-1,5-disulfonic acid salt of 2-[(S)-1-(8-methylaminooctyl)pyrrolidin-3-yl]-2,2-diphenylacetamide of Example 5, about 30 mg each, were stored in multiple 3 mL borosilicate vials at −20° C. (closed container), 40° C./75% RH (open and closed container), and at 80° C. (closed container). At specific intervals, the entire contents of a representative vial was analyzed by the following HPLC method:

Column: Agilent Zorbox SB-C18, 4.6×250 mm, 5 μm (Part No. 880975-902); Mobile Phase A: 98%/2%/0.1% H$_2$O/ACN/TFA; Mobile Phase B: 10%/90%/0.1% H$_2$O/ACN/TFA; Flow rate: 1 mL/min; Injection Volume: 20 μL; Detector: 220 nm; Gradient Time in minutes (% Mobile Phase B): 0.0 (10); 4.00 (20); 26.00 (28); 34.40 (100); 38.40 (100); 38.50 (10); and 45.00 (10).

Samples were prepared as 1 mg/mL solutions using 50% EtOH and 50% citrate buffer (10 mM pH 5 in normal saline). These solutions were then injected onto the HPLC.

The initial purity of the samples was 99.5% as determined by HPLC area percentage. After 3 months of storage, for the samples kept under all conditions, there was no detectable change in chemical purity (less than 0.5%), no observable change in the appearance of the material, and analysis by DSC and TGA showed no detectable differences. Furthermore, there was no detectable chemical or physical differences after 6 months for samples stored at −20° C. (closed container) and 40° C./75% RH (open and closed container).

Example 11

Solution State Stability Assessment

Samples of the crystalline naphthalene-1,5-disulfonic acid salt of 2-[(S)-1-(8-methylaminooctyl)pyrrolidin-3-yl]-2,2-diphenylacetamide of Example 5 were used to prepare an inhalation solution consisting of 1 mg/mL and 0.1 mg/mL salt in normal saline with 10 mM citrate buffer adjusted to pH 5. The resulting solutions were placed in 3 mL borosilicate vials and stoppered with Teflon grey plug stoppers. The solutions were then stored at −20° C., 5° C., 30° C., 60° C. The samples were analyzed according to the HPLC method described in Example 10. After approximately six months for the solutions stored at −20° C., 5° C., and 30° C. there was no detectable change in purity observed (less than 0.5%) for samples stored at 60° C. less than 5% change in purity was observed. There was no appreciable change in pH values of solutions.

Example 12

Elemental Analysis

The following elemental percentages of carbon, hydrogen, nitrogen, and sulfur of a sample of a crystalline naphthalene-1,5-disulfonic acid salt of 2-[(S)-1-(8-methylaminooctyl) pyrrolidin-3-yl]-2,2-diphenylacetamide (prepared according to the procedure of Examples 4 and 5) were determined by combustion analysis using a Flash EA 1112 Elemental Analyzer (CE Elantech, Lakewood, N.J.): carbon 61.65%, hydrogen 6.76% nitrogen 5.83%, sulfur 9.81%.

Example 13

Determination of Counterion Molar Ratio

The molar ratio of naphthalene-1,5-disulfonic acid (NDSA) to 2-[(S)-1-(8-methylaminooctyl)pyrrolidin-3-yl]-2,2-diphenylacetamide (compound I) was calculated from the percentage sulfur content according to the following formula:

$$\text{Molar Ratio} = (W_{NDSA}/MW_{NDSA})/(W_I/MW_I)$$

where $W_{NDSA}$, the weight percentage of NDSA in the sample, is determined from the measured weight percentage of sulfur ($W_S$) in the sample and the weight percentage of sulfur in NDSA (22.24%) as:

$$W_{NDSA} = (W_S/22.24) \times 100;$$

$MW_{NDSA}$ is the molecular weight of NDSA (228.3 amu), $MW_I$ is the molecular weight of compound I (421.6 amu), and $W_I$ is the weight percentage of compound I in the sample, calculated according to the formula:

$$W_I = (100 - W_{NDSA} - W_{H2O} - W_{RS}) \times P$$

where $W_{H2O}$ is the weight percentage water content, $W_{RS}$ is the weight percentage residual solvent, and P is the fractional purity of compound I, as determined by HPLC analysis.

The molar ratio of naphthalene-1,5-disulfonic acid to the compound of formula I for a sample prepared according to the process of Examples 4 and 5 was calculated as 1.17, using the sulfur content Ws of 9.81% from Example 12 above, and the values $W_{H2O}$=0.2%, $W_{RS}$=0.08% and P=0.994. The water content $W_{H2O}$ was determined by coulometric Karl Fisher titration using a Brinkman Metrohm Karl Fisher Model 831 coulometer and the residual solvent content $W_{RS}$ was determined by gas chromatography.

Example 14

Micronization

A sample of a crystalline naphthalene-1,5-disulfonic acid salt of 2-[(S)-1-(8-methylaminooctyl)pyrrolidin-3-yl]-2,2-diphenylacetamide (prepared according to the procedure of Examples 4 and 5) was micronized with a jet mill to give a free-flowing white powder with birefringence observed upon microscopic examination. Particle size analysis showed that 99.5% of particles based on volume had a particle size of less than 10 µm; 80% had a particle size less than 5 µm; and 50% had a particle size less than 3 µm. No change was observed in the PXRD pattern, TGA trace, DSC trace, DMS trace, chemical purity, chiral purity and moisture content for the micronized material compared to the unmicronized material.

Example 15

Micronized Salt/Micronized Salt-Lactose Blend Stability Assessment

A sample of micronized crystalline naphthalene-1,5-disulfonic acid salt of 2-[(S)-1-(8-methylaminooctyl)pyrrolidin-3-yl]-2,2-diphenylacetamide of Example 14, was blended with lactose (Respitose ML001, DMV International) at 0.1%, 0.3%, and 3% weight-by-weight micronized salt to lactose strengths. The resulting blends had excellent content uniformity with relative standard deviation of less than 2%.

Approximately 100 mg of the neat salt and micronized salt and 300 mg of the three different strengths of lactose blends were stored in multiple 3 mL borosilicate vials at −20° C. (closed container) and 40° C./75% RH (open and closed container), and 50° C. (closed container). At specific intervals, appropriate amount of the sample was diluted with 10 mM citrate pH 5 Normal saline solution to achieve a concentration of approximately 1 mg/mL, 20 microliters of the resulting solution was then injected and analyzed by the following HPLC method:

Column: Aglient Zorbax SB-C18 4.6×250 mm, 5 µm; Mobile phase A: 98%/2%/0.1% $H_2O$/ACN/TFA; Mobile Phase B: 10%/90%/0.1% $H_2O$/ACN/TFA; Flow rate 1 mL/min; Detector 240 nm; Gradient time in minutes (% mobile phase B): 0.0 (10); 4.0 (20); 31.0 (24); 39.4 (100); 43.4 (100); 43.5 (10); 50.0 (10).

The initial purity of the neat salt form was 99.8% as determined by HPLC area percent. After 3 months of storage for all the samples tested (neat salt form, micronized salt form, 0.1% micronized salt with lactose blend, 0.3% micronized salt with lactose blend, 3% micronized salt with lactose blend) under all the storage conditions (−20° C. closed, 40° C./75% RH open and closed, 50 C closed) there was no detectable change in chemical purity (less than 0.5%) Furthermore, all the samples and blends tested remained free flowing white powder after three months storage under the conditions stated above.

Assay 1

Radioligand Binding Assay

A. Membrane Preparation from Cells Expressing $hM_1$, $hM_2$, $hM_3$ and $hM_4$ Muscarinic Receptor Subtypes CHO cell lines stably expressing cloned human $hM_1$, $hM_2$, $hM_3$ and $hM_4$ muscarinic receptor subtypes, respectively, were grown to near confluency in medium consisting of HAM's F-12 supplemented with 10% FBS and 250 µg/mL Geneticin. The cells were grown in a 5% $CO_2$, 37° C. incubator and lifted with 2 mM EDTA in dPBS. Cells were collected by 5 minute centrifugation at 650×g, and cell pellets were either stored frozen at −80° C. or membranes were prepared immediately. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with resuspension buffer and homogenized again with the Polytron tissue disrupter. The protein concentration of the membrane suspension was determined by the method described in Lowry, O. et al., *Journal of Biochemistry* 193:265 (1951). All membranes were stored frozen in aliquots at −80° C. or used immediately. Aliquots of prepared $hM_5$ receptor membranes were purchased directly from Perkin Elmer and stored at −80° C. until use.

B. Radioligand Binding Assay on Muscarinic Receptor Subtypes $hM_1$, $hM_2$, $hM_4$, and $hM_5$ Radioligand binding assays were performed in 96-well microtiter plates in a total assay volume of 100 µL. CHO cell membranes stably expressing either the $hM_1$, $hM_2$, $hM_3$, $hM_4$ or $hM_5$ muscarinic subtype were diluted in assay buffer to the following specific target protein concentrations (µg/well): 10

μg for $hM_1$, 10-15 μg for $hM_2$, 10-20 μg for $hM_3$, 10-20 μg for $hM_4$, and 10-12 μg for $hM_5$. The membranes were briefly homogenized using a Polytron tissue disruptor (10 seconds) prior to assay plate addition. Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 400 μM in dilution buffer and then serially diluted 5× with dilution buffer to final concentrations ranging from 10 pM to 100 μM. The addition order and volumes to the assay plates were as follows: 25 μL radioligand, 25 μL diluted test compound, and 50 μL membranes. Assay plates were incubated for 60 minutes at 37° C. Binding reactions were terminated by rapid filtration over GF/B glass fiber filter plates (PerkinElmer Inc., Wellesley, Mass.) pre-treated in 1% BSA. Filter plates were rinsed three times with wash buffer (10 mM HEPES) to remove unbound radioactivity. Plates were then air dried, and 50 μL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W H. *Biochemical Pharmacology*, 22(23):3099-108 (1973)). $K_i$ values were converted to $pK_i$ values to determine the geometric mean and 95% confidence intervals. These summary statistics were then converted back to $K_i$ values for data reporting.

In this assay, a lower $K_i$ value indicates that a test compound has a higher binding affinity for the receptor tested. The compound of formula I was found to have a $K_i$ value of about 0.96 nM for the $M_3$ muscarinic receptor subtype in this assay.

Assay 2

Muscarinic Receptor Functional Potency Assays

A. Blockade of Agonist-Mediated Inhibition of cAMP Accumulation

In this assay, the functional potency of a test compound was determined by measuring the ability of the test compound to block oxotremorine-inhibition of forskolin-mediated cAMP accumulation in CHO-K1 cells expressing the $hM_2$ receptor.

cAMP assays were performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions.

Cells were rinsed once with dPBS and lifted with Trypsin-EDTA solution (0.05% trypsin/0.53 mM EDTA) as described in the Cell Culture and Membrane Preparation section above. The detached cells were washed twice by centrifugation at 650×g for five minutes in 50 mLs dPBS. The cell pellet was then re-suspended in 10 mL dPBS, and the cells were counted with a Coulter Z1 Dual Particle Counter (Beckman Coulter, Fullerton, Calif.). The cells were centrifuged again at 650×g for five minutes and re-suspended in stimulation buffer to an assay concentration of 1.6×10$^6$-2.8×10$^6$ cells/mL.

The test compound was initially dissolved to a concentration of 400 μM in dilution buffer (dPBS supplemented with 1 mg/mL BSA (0.1%)), and then serially diluted with dilution buffer to final molar concentrations ranging from 100 μM to 0.1 nM. Oxotremorine was diluted in a similar manner.

To measure oxotremorine inhibition of AC activity, 25 μL forskolin (25 μM final concentration diluted in dPBS), 25 μL diluted oxotremorine, and 50 μL cells were added to agonist assay wells. To measure the ability of a test compound to block oxotremorine-inhibited AC activity, 25 μL forskolin and oxotremorine (25 μM and 5 μM final concentrations, respectively, diluted in dPBS) 25 μL diluted test compound, and 50 μL cells were added to remaining assay wells.

Reactions were incubated for 10 minutes at 37° C. and stopped by addition of 100 μL ice-cold detection buffer. Plates were sealed, incubated overnight at room temperature and counted the next morning on a PerkinElmer TopCount liquid scintillation counter (PerkinElmer Inc., Wellesley, Mass.). The amount of cAMP produced (pmol/well) was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $EC_{50}$ of the oxotremorine concentration-response curve and the oxotremorine assay concentration as the $K_D$ and [L], respectively. The $K_i$ values were converted to $pK_i$ values to determine the geometric mean and 95% confidence intervals. These summary statistics were then converted back to $K_i$ values for data reporting.

In this assay, a lower $K_i$ value indicates that a test compound has a higher functional activity at the receptor tested. The compound of formula I was found to have a $K_i$ value of less than 5 nM for blockade of oxotremorine-inhibition of forskolin-mediated cAMP accumulation in CHO-K1 cells expressing the $hM_2$ receptor.

B. Blockade of Agonist-Mediated [$^{35}$S]GTPγS Binding

In a second functional assay, the functional potency of a test compound is determined by measuring the ability of the compound to block oxotremorine-stimulated [$^{35}$S]GTPγS binding in CHO-K1 cells expressing the $hM_2$ receptor.

At the time of use, frozen membranes were thawed and then diluted in assay buffer with a final target tissue concentration of 5-10 μg protein per well. The membranes were briefly homogenized using a Polytron PT-2100 tissue disrupter and then added to the assay plates.

The $EC_{90}$ value (effective concentration for 90% maximal response) for stimulation of [$^{35}$S]GTPγS binding by the agonist oxotremorine was determined in each experiment.

To determine the ability of a test compound to inhibit oxotremorine-stimulated [$^{35}$S]GTPγS binding, the following was added to each well of 96 well plates: 25 μL of assay buffer with [$^{35}$S]GTPγS (0.4 nM), 25 μL of oxotremorine ($EC_{90}$) and GDP (3 uM), 25 μL of diluted test compound and 25 μL CHO cell membranes expressing the $hM_2$ receptor. The assay plates were then incubated at 37° C. for 60 minutes. The assay plates were filtered over 1% BSA-pretreated GF/B filters using a PerkinElmer 96-well harvester. The plates were rinsed with ice-cold wash buffer for 3×3 seconds and then air or vacuum dried. Microscint-20 scintillation liquid (50 μL) was added to each well, and each plate was sealed and radioactivity counted on a topcounter (PerkinElmer). Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $IC_{50}$ values of the concentration-response curve for the test compound and the oxotremorine concentration in the assay as the $K_D$ and [L], ligand concentration, respectively.

In this assay, a lower $K_i$ value indicates that a test compound has a higher functional activity at the receptor tested. The compound of formula I was found to have a $K_i$ value of less than 5 nM for blockade of oxotremorine-stimulated [$^{35}$S] GTPγS binding in CHO-K1 cells expressing the $hM_2$ receptor.

C. Blockade of Agonist-Mediated Calcium Release Via FLIPR Assays

Muscarinic receptor subtypes ($M_1$, $M_3$ and $M_5$ receptors), which couple to $G_q$ proteins, activate the phospholipase C (PLC) pathway upon agonist binding to the receptor. As a result, activated PLC hydrolyzes phosphatyl inositol diphosphate ($PIP_2$) to diacylglycerol (DAG) and phosphatidyl-1,4, 5-triphosphate ($IP_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event is measured in real time by the FLIPR, which detects the change in fluorescence from a monolayer of cells cloned with human $M_1$ and $M_3$, and chimpanzee $M_5$ receptors. Antagonist potency is determined by the ability of antagonists to inhibit agonist-mediated increases in intracellular calcium.

For FLIPR calcium stimulation assays, CHO cells stably expressing the $hM_1$, $hM_3$ and $cM_5$ receptors were seeded into 96-well FLIPR plates the night before the assay was done. Seeded cells were washed twice by Cellwash (MTX Labsystems, Inc.) with FLIPR buffer (10 mM HEPES, pH 7.4, 2 mM calcium chloride, 2.5 mM probenecid in HBSS without calcium and magnesium) to remove growth media and leave 50 μL/well of FLIPR buffer. The cells were then incubated with 50 μL/well of 4 μM FLUO-4 AM (a 2× solution was made) for 40 minutes at 37° C., 5% carbon dioxide. Following the dye incubation period, cells were washed two times with FLIPR buffer, leaving a final volume of 50 μL/well.

To determine antagonist potency, the dose-dependent stimulation of intracellular $Ca^{2+}$ release for oxotremorine was first determined so that antagonist potency can later be measured against oxotremorine stimulation at an $EC_{90}$ concentration. Cells were first incubated with compound dilution buffer for 20 minutes, followed by agonist addition, which was performed by the FLIPR. An $EC_{90}$ value for oxotremorine was generated according to the method detailed in the FLIPR measurement and data reduction section below, in conjunction with the formula $EC_F=((F/100-F)^{1/H})*EC_{50}$. An oxotremorine concentration of $3 \times EC_F$ was prepared in stimulation plates such that an $EC_{90}$ concentration of oxotremorine was added to each well in the antagonist inhibition assay plates.

The parameters used for the FLIPR were: exposure length of 0.4 seconds, laser strength of 0.5 watts, excitation wavelength of 488 nm, and emission wavelength of 550 nm. Baseline was determined by measuring the change in fluorescence for 10 seconds prior to addition of agonist. Following agonist stimulation, the FLIPR continuously measured the change of fluorescence every 0.5 to 1 second for 1.5 minutes to capture the maximum fluorescence change.

The change of fluorescence was expressed as maximum fluorescence minus baseline fluorescence for each well. The raw data was analyzed against the logarithm of drug concentration by nonlinear regression with GraphPad Prism (GraphPad Software, Inc., San Diego, Calif.) using the built-in model for sigmoidal dose-response. Antagonist $K_i$ values were determined by Prism using the oxotremorine $EC_{50}$ value as the $K_D$ and the oxotremorine $EC_{90}$ for the ligand concentration according to the Cheng-Prusoff equation (Cheng Y; Prusoff W. H. *Biochemical Pharmacology* 22(23):3099-108 (1973)).

In this assay, a lower $K_i$ value indicates that a test compound has a higher functional activity at the receptor tested. The compound of formula I was found to have a $K_i$ value of less than 5 nM for blockade of agonist-mediated calcium release in CHO cells stably expressing the $hM_3$ receptor.

Assay 3

Determination of Duration of Bronchoprotection in Guinea Pig Model of Acetylcholine-Induced Bronchoconstriction This in vivo assay was used to assess the bronchoprotective effects of test compounds exhibiting muscarinic receptor antagonist activity.

Groups of six male guinea pigs (Duncan-Hartley (HsdPoc: DH) Harlan, Madison, Wis.) weighing between 250 and 350 g were individually identified by cage cards. Throughout the study animals were allowed access to food and water ad libitum.

The test compound was administered via inhalation over 10 minutes in a whole-body exposure dosing chamber (R&S Molds, San Carlos, Calif.). The dosing chambers were arranged so that an aerosol was simultaneously delivered to 6 individual chambers from a central manifold. Guinea pigs were exposed to an aerosol of a test compound or vehicle (WFI). These aerosols were generated from aqueous solutions using an LC Star Nebulizer Set (Model 22F51, PARI Respiratory Equipment, Inc. Midlothian, Va.) driven by a mixture of gases ($CO_2$=5%, $O_2$=21% and $N_2$=74%) at a pressure of 22 psi. The gas flow through the nebulizer at this operating pressure was approximately 3 L/minute. The generated aerosols were driven into the chambers by positive pressure. No dilution air was used during the delivery of aerosolized solutions. During the 10 minute nebulization, approximately 1.8 mL of solution was nebulized. This was measured gravimetrically by comparing pre-and post-nebulization weights of the filled nebulizer.

The bronchoprotective effects of a test compound administered via inhalation were evaluated using whole body plethysmography at 1.5, 24, 48 and 72 hours post-dose.

Forty-five minutes prior to the start of the pulmonary evaluation, each guinea pig was anesthetized with an intramuscular injection of ketamine (43.75 mg/kg), xylazine (3.50 mg/kg) and acepromazine (1.05 mg/kg). After the surgical site was shaved and cleaned with 70% alcohol, a 2-3 cm midline incision of the ventral aspect of the neck was made. Then, the jugular vein was isolated and cannulated with a saline-filled polyethylene catheter (PE-50, Becton Dickinson, Sparks, Md.) to allow for intravenous infusions of Ach (Sigma, St. Louis, Mo.) in saline. The trachea was then dissected free and cannulated with a 14G teflon tube (#NE-014, Small Parts, Miami Lakes, Fla.). If required, anesthesia was maintained by additional intramuscular injections of the aforementioned anesthetic mixture. The depth of anesthesia was monitored and adjusted if the animal responded to pinching of its paw or if the respiration rate was greater than 100 breaths/minute.

Once the cannulations were complete, the animal was placed into a plethysmograph (#PLY3114, Buxco Electronics, Inc., Sharon, Conn.) and an esophageal pressure cannula (PE-160, Becton Dickinson, Sparks, Md.) was inserted to measure pulmonary driving pressure (pressure). The teflon tracheal tube was attached to the opening of the plethysmograph to allow the guinea pig to breathe room air from outside the chamber. The chamber was then sealed. A heating lamp was used to maintain body temperature and the guinea pig's lungs were inflated 3 times with 4 mL of air using a 10 mL calibration syringe (#5520 Series, Hans Rudolph, Kansas City, Mo.) to ensure that the lower airways did not collapse and that the animal did not suffer from hyperventilation.

Once it was determined that baseline values were within the range 0.3-0.9 mL/cm $H_2O$ for compliance and within the range 0.1-0.199 cm $H_2O$/mL per second for resistance, the pulmonary evaluation was initiated. A Buxco pulmonary measurement computer program enabled the collection and derivation of pulmonary values.

Starting this program initiated the experimental protocol and data collection. The changes in volume over time that occur within the plethysmograph with each breath were measured via a Buxco pressure transducer. By integrating this signal over time, a measurement of flow was calculated for each breath. This signal, together with the pulmonary driving pressure changes, which were collected using a Sensym pressure transducer (#TRD4100), was connected via a Buxco (MAX 2270) preamplifier to a data collection interface (#'s SFT3400 and SFT3813). All other pulmonary parameters were derived from these two inputs.

Baseline values were collected for 5 minutes, after which time the guinea pigs were challenged with Ach. Ach (Sigma-Aldrich, St. Louis, Mo.) (0.1 mg/mL) was infused intravenously for 1 minute from a syringe pump (sp210iw, World Precision Instruments, Inc., Sarasota, Fla.) at the following doses and prescribed times from the start of the experiment: 1.9 µg/minute at 5 minutes, 3.8 µg/minute at 10 minutes, 7.5 µg/minute at 15 minutes, 15.0 µg/minute at 20 minutes, 30 µg/minute at 25 minutes and 60 µg/minute at 30 minutes. If resistance or compliance had not returned to baseline values at 3 minutes following each Ach dose, the guinea pig's lungs were inflated 3 times with 4 mL of air from a 10 mL calibration syringe. Recorded pulmonary parameters included respiration frequency (breaths/minute), compliance (mL/cm $H_2O$) and pulmonary resistance (cm $H_2O$/mL per second). Once the pulmonary function measurements were completed at minute 35 of this protocol, the guinea pig was removed from the plethysmograph and euthanized by carbon dioxide asphyxiation.

The data were evaluated in one or both of the following ways:

(a) Pulmonary resistance ($R_L$, cm $H_2O$/mL per second) was calculated from the ratio of "change in pressure" to "the change in flow." The $R_L$ response to ACh (60 µg/min, IH) was computed for the vehicle and the test compound groups. The mean ACh response in vehicle-treated animals, at each pre-treatment time, was calculated and used to compute % inhibition of ACh response, at the corresponding pre-treatment time, at each test compound dose. Inhibition dose-response curves for '$R_L$' were fitted with a four parameter logistic equation using GraphPad Prism, version 3.00 for Windows (GraphPad Software, San Diego, Calif.) to estimate bronchoprotective $ID_{50}$ (dose required to inhibit the ACh (60 µg/min) bronchoconstrictor response by 50%). The equation used was as follows:

$$Y = Min + (Max - Min)/(1 + 10^{((\log ID50 - X)*Hillslope)})$$

where X is the logarithm of dose, Y is the response (% Inhibition of ACh induced increase in $R_L$). Y starts at Min and approaches asymptotically to Max with a sigmoidal shape.

(b) The quantity $PD_2$, which is defined as the amount of Ach or histamine needed to cause a doubling of the baseline pulmonary resistance, was calculated using the pulmonary resistance values derived from the flow and the pressure over a range of Ach or histamine challenges using the following equation (which is derived from a equation used to calculate $PC_{20}$ values described in American Thoracic Society. Guidelines for methacholine and exercise challenge testing—1999. *Am J Respir Crit Care Med.* 161: 309-329 (2000)):

$$PD_2 = \text{antilog}\left[\log C_1 + \frac{(\log C_2 - \log C_1)(2R_0 - R_1)}{R_2 - R_1}\right]$$

where:
$C_1$=concentration of ACh or histamine preceding $C_2$
$C_2$=concentration of ACh or histamine resulting in at least a 2-fold increase in pulmonary resistance ($R_L$)
$R_0$=Baseline $R_L$ value
$R_1$=$R_L$ value after $C_1$
$R_2$=$R_L$ value after $C_2$ An efficacious dose was defined as a dose that limited the bronchrestriction response to a 50 µg/mL dose of Ach to a doubling of the baseline pulmonary resistance ($PD_{2(50)}$). Statistical analysis of the data was performed using a two-tailed Students t-test. A P-value <0.05 was considered significant.

Generally, a test compound having a $PD_{2(50)}$ less than about 200 µg/mL for ACh-induced bronchoconstriction at 1.5 hours post-dose in this assay is preferred. The compound of formula I was found to have a $PD_{2(50)}$ less than about 200 µg/mL for ACh-induced bronchoconstriction at 1.5 hours post-dose.

Assay 4

Inhalation Guinea Pig Salivation Assay

Guinea pigs (Charles River, Wilmington, Mass.) weighing 200-350 g were acclimated to the in-house guinea pig colony for at least 3 days following arrival. Test compound or vehicle were dosed via inhalation (IH) over a 10 minute time period in a pie shaped dosing chamber (R+S Molds, San Carlos, Calif.). Test solutions were dissolved in sterile water and delivered using a nebulizer filled with 5.0 mL of dosing solution. Guinea pigs were restrained in the inhalation chamber for 30 minutes. During this time, guinea pigs were restricted to an area of approximately 110 cm². This space was adequate for the animals to turn freely, reposition themselves, and allow for grooming. Following 20 minutes of acclimation, guinea pigs were exposed to an aerosol generated from a LS Star Nebulizer Set (Model 22F51, PARI Respiratory Equipment, Inc. Midlothian, Va.) driven by house air at a pressure of 22 psi. Upon completion of nebulization, guinea pigs were evaluated at 1.5, 6, 12, 24, 48, or 72 hrs after treatment.

Guinea pigs were anesthetized one hour before testing with an intramuscular (IM) injection of a mixture of ketamine 43.75 mg/kg, xylazine 3.5 mg/kg, and acepromazine 1.05 mg/kg at an 0.88 mL/kg volume. Animals were placed ventral side up on a heated (37° C.) blanket at a 20 degree incline with their head in a downward slope. A 4-ply 2×2 inch gauze pad (Nu-Gauze General-use sponges, Johnson and Johnson, Arlington, Tex.) was inserted in the guinea pig's mouth. Five minutes later, the muscarinic agonist pilocarpine (3.0 mg/kg, s.c.) was administered and the gauze pad was immediately discarded and replaced by a new pre-weighed gauze pad. Saliva was collected for 10 minutes, at which point the gauze pad was weighed and the difference in weight recorded to determine the amount of accumulated saliva (in mg). The mean amount of saliva collected for animals receiving the vehicle and each dose of test compound was calculated. The vehicle group mean was considered to be 100% salivation. Results were calculated using result means (n=3 or greater). Confidence intervals (95%) were calculated for each dose at each time point using two-way ANOVA. This model is a modified version of the procedure described in Rechter, "Estimation of anticholinergic drug effects in mice by antagonism against pilocarpine-induced salivation" *Ata Pharmacol Toxicol* 24:243-254 (1999).

The mean weight of saliva in vehicle-treated animals, at each pre-treatment time, was calculated and used to compute % inhibition of salivation, at the corresponding pre-treatment time, at each dose. The inhibition dose-response data were fitted to a four parameter logistic equation using GraphPad Prism, version 3.00 for Windows (GraphPad Software, San Diego, Calif.) to estimate anti-sialagogue $ID_{50}$ (dose required to inhibit 50% of pilocarpine-evoked salivation). The equation used was as follows:

$$Y = Min + (Max - Min)/(1 + 10^{(\log ID50 - X) \cdot Hillslope})$$

where X is the logarithm of dose, Y is the response (% inhibition of salivation). Y starts at Min and approaches asymptotically to Max with a sigmoidal shape.

The ratio of the anti-sialagogue $ID_{50}$ to bronchoprotective $ID_{50}$ was used to compute the apparent lung selectivity index of the test compound. Generally, compounds having an apparent lung selectivity index greater than about 5 are preferred. In this assay, the compound of formula I had an apparent lung-selectivity index greater than about 5.

Assay 5

Methacholine-Induced Depressor Responses in Conscious Guinea Pigs

Healthy, adult, male Sprague-Dawley guinea pigs (Harlan, Indianapolis, Ind.), weighing between 200 and 300 g were used in these studies. Under isoflurane anesthesia (to effect), animals were instrumented with common carotid artery and jugular vein catheters (PE-50 tubing). The catheters were exteriorized utilizing a subcutaneous tunnel to the subscapular area. All surgical incisions were sutured with 4-0 Ethicon Silk and the catheters locked with heparin (1000 units/mL). Each animal was administered saline (3 mL, SC) at the end of surgery as well as buprenorphine (0.05 mg/kg, IM). Animals were allowed to recover on a heating pad before being returned to their holding rooms.

Approximately 18 to 20 hours following surgery, the animals were weighed and the carotid artery catheter on each animal was connected to a transducer for recording arterial pressure. Arterial pressure and heart rate was recorded using a Biopac MP-100 Acquisition System. Animals were allowed to acclimate and stabilize for a period of 20 minutes.

Each animal was challenged with methylcholine (MCh) (0.3 mg/kg, iv) administer through the jugular venous line and the cardiovascular response was monitored for 10 minutes. The animals were then placed into the whole body dosing chamber, which was connected to a nebulizer containing the test compound or vehicle solution. The solution was nebulized for 10 minutes using a gas mixture of breathable air and 5% carbon dioxide with a flow rate of 3 liters/minute. The animals were then removed from the whole body chamber and returned to their respective cages. At 1.5 and 24 h post-dosing, the animals were re-challenged with MCh (0.3 mg/kg, iv) and the hemodynamic response was determined. Thereafter, the animals were euthanized with sodium pentobarbital (150 mg/kg, IV).

MCh produces a decrease in mean arterial pressure (MAP) and decrease in heart rate (bradycardia). The peak decrease, from baseline, in MAP (depressor responses) was measured for each MCh challenge (before and after IH dosing). The bradycardic effects were not used for analysis since these responses were not robust and reproducible. The effects of treatment on the MCh responses are expressed as % inhibition (mean+/−SEM) of the control depressor responses. Two-way ANOVA with the appropriate post-hoc test was used to test the effects of treatment and pre-treatment time. The depressor responses to MCh were relatively unchanged at 1.5 and 24 h after inhalation dosing with vehicle.

The ratio of the anti-depressor $ID_{50}$ to bronchoprotective $ID_{50}$ was used to compute apparent lung-selectivity of the test compound. Generally, compounds having an apparent lung-selectivity index greater than 5 are preferred. In this assay, the compound of Example 1 had an apparent lung-selectivity index greater than 5.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A crystalline naphthalene-1,5-disulfonic acid salt of 2-[(S)-1-(8-methylaminooctyl)pyrrolidin-3-yl]-2,2-diphenylacetamide characterized by at least one of (i) a powder x-ray diffraction pattern having two or more diffraction peaks at 2θ values selected from 5.45±0.2, 8.17±0.2, 12.02±0.2, 13.46±0.2, 14.00±0.2, 14.46±0.2, 15.69±0.2, 16.31±0.2, 17.22±0.2, 18.45±0.2, 20.13±0.2, 21.11±0.2, and 21.62±0.2; (ii) a differential scanning calorimetry trace which shows an onset of endothermic heat flow at about 200° C.; and (iii) an infrared absorption spectrum with significant absorption bands at about 696, 704, 765, 800, 1028, 1154, 1172, 1191, 1217, 1230, 1245, and 1669 cm$^{-1}$.

2. The compound of claim 1, wherein the compound is characterized by a powder x-ray diffraction pattern having two or more diffraction peaks at 2θ values selected from 5.45±0.2, 8.17±0.2, 12.02±0.2, 13.46±0.2, 14.00±0.2, 14.46±0.2, 15.69±0.2, 16.31±0.2, 17.22±0.2, 18.45±0.2, 20.13±0.2, 21.11±0.2, and 21.62±0.2.

3. The compound of claim 2, wherein the powder x-ray diffraction pattern comprises diffraction peaks at 2θ values of 8.17±0.2, 12.02±0.2, and 17.22±0.2.

4. The compound of claim 1, wherein the compound is characterized by a powder x-ray diffraction pattern in which the peak positions are substantially in accordance with the peak positions of the pattern shown in FIG. 1.

5. The compound of claim 1, wherein the compound is characterized by a differential scanning calorimetry trace which shows an onset of endothermic heat flow at about 200° C.

6. The compound of claim 1, wherein the compound is characterized by a differential scanning calorimetry trace substantially in accordance with that shown in FIG. 2.

7. The compound of claim 1, wherein the compound has an infrared absorption spectrum with significant absorption bands at about 696, 704, 765, 800, 1028, 1154, 1172, 1191, 1217, 1230, 1245, and 1669 cm$^{-1}$.

8. The compound of claim 1, wherein the compound is characterized by an infrared absorption spectrum substantially in accordance with that shown in FIG. 4.

9. The crystalline naphthalene-1,5-disulfonic acid salt of claim 1, in micronized form.

10. A process for preparing the crystalline naphthalene-1,5-disulfonic acid salt of claim 1; the process comprising contacting 2-[(S)-1-(8-methylaminooctyl)pyrrolidin-3-yl]-2,2-diphenylacetamide dissolved in isopropanol with about 0.75 to about 1.3 molar equivalents 1,5-naphthalenedisulfonic acid dissolved in ethanol and water or isopropanol and water, to form a mixture; heating the mixture to between about 25° C. to about 50° C.; and cooling the mixture to room temperature to form the crystalline naphthalene-1,5-disulfonic acid salt of 2-[(S)-1-(8-methylaminooctyl)pyrrolidin-3-yl]-2,2-diphenylacetamide.

11. A process for preparing the crystalline naphthalene-1,5-disulfonic acid salt of claim 1; the process comprising contacting 2-{(S)-1-[8-(N-tert-butoxycarbonyl-N-methylamino)-octyl]pyrrolidin-3-yl}-2,2-diphenylacetamide with about 1 to about 2.1 molar equivalents 1,5-naphthalenedisulfonic acid dissolved in isopropanol and water, to form a mixture; heating the mixture to between about 70° C.; to about 90° C.; and cooling the mixture to room temperature to form the crystalline naphthalene-1,5-disulfonic acid salt of 2-[(S)-1-(8-methylaminooctyl)pyrrolidin-3-yl]-2,2-diphenylacetamide.

12. A process for purifying 2-[(S)-1-(8-methylaminooctyl)pyrrolidin-3-yl]-2,2-diphenylacetamide; the process comprising forming the crystalline naphthalene-1,5-disulfonic acid salt of claim 1 by:

contacting 2-[(S)-1-(8-methylaminooctyl)pyrrolidin-3-yl]-2,2-diphenylacetamide dissolved in isopropanol with about 0.75 to about 1.3 molar equivalents 1,5-naphthalenedisulfonic acid dissolved in ethanol and water or isopropanol and water, to form a mixture; heating the mixture to between about 25° C. to about 50° C.; and cooling the mixture to room temperature to form the crystalline naphthalene-1,5-disulfonic acid salt of 2-[(S)-1-(8-methylaminooctyl)pyrrolidin-3-yl]-2,2-diphenylacetamide or contacting 2-{(S)-1-[8-(N-tert-butoxycarbonyl-N-methylamino)-octyl]pyrrolidin-3-yl}-2,2-diphenylacetamide with about 1 to about 2.1 molar equivalents 1,5-naphthalenedisulfonic acid dissolved in isopropanol and water, to form a mixture; heating the mixture to between about 70° C. to about 90° C.; and cooling the mixture to room temperature to form the crystalline naphthalene-1,5-disulfonic acid salt of 2-[(S)-1-(8-methylaminooctyl)pyrrolidin-3-yl]-2,2-diphenylacetamide.

13. The product prepared by the process of any one of claims 10, 11 or 12.

\* \* \* \* \*